US006174713B1

(12) United States Patent
Shen et al.

(10) Patent No.: US 6,174,713 B1
(45) Date of Patent: Jan. 16, 2001

(54) CANDIDA CYTOPLASMIC TRYPTOPHANYL-TRNA SYNTHETASE PROTEINS, NUCLEIC ACIDS AND STRAINS COMPRISING SAME

(75) Inventors: Xiaoyu Shen, Boston; Fariba Houman, Belmont, both of MA (US)

(73) Assignee: Cubist Pharmaceuticals, Inc., Cambridge, MA (US)

( * ) Notice: Under 35 U.S.C. 154(b), the term of this patent shall be extended for 0 days.

(21) Appl. No.: 08/876,885

(22) Filed: Jun. 16, 1997

(51) Int. Cl.[7] .............................. C12N 9/00; C12N 1/20; C12Q 1/68; C07H 21/04
(52) U.S. Cl. ......................... 435/183; 435/6; 435/252.3; 435/254.11; 435/325; 435/320.1; 536/23.2; 536/24.3
(58) Field of Search ........................... 435/183, 6, 252.3, 435/254.11, 325, 320.1; 536/23.2, 24.3

(56) References Cited

U.S. PATENT DOCUMENTS

| 4,713,337 | 12/1987 | Jasin et al. ........................ 435/172.3 |
| 4,788,148 | 11/1988 | Nilsson et al. ....................... 435/320 |
| 4,952,501 | 8/1990 | Jasin et al. .......................... 435/69.2 |
| 4,963,487 | 10/1990 | Schimmel et al. ................. 435/172.3 |
| 5,370,995 | 12/1994 | Hennecke et al. .................. 435/69.1 |
| 5,561,054 | 10/1996 | Kron et al. ........................... 435/69.1 |
| 5,656,470 | 8/1997 | Martinis et al. ...................... 435/183 |
| 5,688,655 | 11/1997 | Housey et al. ....................... 435/7.21 |

FOREIGN PATENT DOCUMENTS

WO 95/09927   4/1995   (WO).

OTHER PUBLICATIONS

Partial DNA sequence of *Candida albicans* gene having DNA sequence homology to *Saccharomyces cerevisiae* MSW1 (mitochondrial tryptophanyl–tRNA synthetase). *Candida albicans* information page: http://alces.med.umn.edu/candida/oursegs/L–5HR.Seq. Date of public availability: Jan. 18, 1995.

Meinnel, T., et al., "Aminoacyl–tRNA Synthetases: Occurrence, Structure and Function." In tRNA: Structure, Biosynthesis, and Function, Söll, D. and RajBhandary, U., eds. (Washington, DC: American Society for Microbiology), pp. 251–300 (1995).

von der Haar, F. et al, "Target Directed Drug Synthesis: The Aminoacyl–tRNA Synthetases as Possible Targets," *Agew. Chem. Int. Ed. Engl.*, 20(3) :217–223 (1981).

Walter, R. D. and Kuhlow, F., "Parasite–Specific Interaction of N–[4–(4'Nitroanilino–Phenyl]–S–(β–Carboxyethyl)–Dithiocarbamic Acid–Ester with Arginyl–tRNA–Synthetase from *Dirofilaria immitis*," *Trop. Med. Parasit.*, 36:230–232 (1985).

Hughes, J., et al., "Inhibition of Isoleucyl–Transfer Ribonucleic Acid Synthetase in *Escherichia coli* by Pseudomonic Acid," *Biochem. J.*, 176:305–318 (1978).

Hughes, J. and Mellows, G., "Interaction of Pseudomonic Acid A with *Escherichia coli* B Isoleucyl–tRNA Synthetase," *Biochem J.*, 191:209–219 (1980).

Shiba, K. and Shimmel, P., "Functional Assembly of a Randomly Cleaved Protein," *Proc. Natl. Acad. Sci. USA*, 89:1880–1884 (1992).

Shepard, A., et al., "RNA Binding Determinant in Some Class I tRNA Synthetases Identified by Alignment–Guided Mutagenesis," *Proc. Natl. Acad. Sci. USA*, 89:9964–9968 (1992).

Kim, S., et al., "Diversified Sequences of Peptide Epitope for Same–RNA Recognition," *Proc. Natl. Acad. Sci. USA*, 90:10046–10050 (1993).

Edwards, H., et al., "An *E. coli* Aminoacyl–tRNA Synthetase Can Substitute for Yeast Mitochondrial Enzyme Function In Vivo," *Cell*, 51:643–649 (1987).

Edwards, H. and Schimmel, P., "A Bacterial Amber Suppressor in *Saccharomyces cerevisiae* Is Selectively Recognized by a Bacterial Aminoacyl–tRNA Synthetase," *Mol. Cell. Biol.*, 10(4) :1633–1641 (1990).

Weygand–Durašević, I., et al., "Yeast Seryl–tRNA Synthetase Expressed in *Escherichia coli* Recognizes Bacterial Serine–Specific tRNAs in vivo," *Eur. J. Biochem.*, 214:869–877 (1993).

Jones, M. D., et al., "Natural Variation of Tyrosyl–tRNA Synthetase and Comparison with Engineered Mutants," *Biochemistry*, 25:1887–1891 (1986).

Suzuki, Tsutomu, et al., 'The Polysemous' Codon—A Codon with Multiple Amino Acid Assignment Caused by Dual Specificity of tRNA Identity, *The EMBO Journal*, 16(5) :1122–1134 (1997).

(List continued on next page.)

Primary Examiner—Lisa J. Hobbs
(74) Attorney, Agent, or Firm—Hamilton, Brook, Smith & Reynolds, P.C.

(57) ABSTRACT

The present invention relates to isolated and/or recombinant nucleic acids which encode Candida cytoplasmic tryptophanyl-tRNA synthetases, portions thereof, or fusion proteins comprising a Candida cytoplasmic tryptophanyl-tRNA synthetase or portion thereof. Also disclosed are constructs comprising the nucleic acids of the present invention, host cells comprising a recombinant nucleic acid or construct, and methods of producing a Candida cytoplasmic tryptophanyl-tRNA synthetase, portion thereof, or fusion protein comprising the same. Also described are tester strains, which are cells engineered to rely on the function of a Candida cytoplasmic tryptophanyl-tRNA synthetase or functional fragment thereof encoded by an introduced cloned gene, and which can be used in a method of detecting an inhibitor of Candida cytoplasmic tryptophanyl-tRNA synthetase function. The invention further relates to isolated and/or recombinant Candida cytoplasmic tryptophanyl-tRNA synthetases, portions thereof, or fusion proteins comprising a Candida cytoplasmic tryptophanyl-tRNA synthetase or portion thereof, methods of use of these polypeptides in an assay to identify inhibitors of Candida cytoplasmic tryptophanyl-tRNA synthetase function, and antibodies reactive with Candida cytoplasmic tryptophanyl-tRNA synthetases.

19 Claims, 3 Drawing Sheets

OTHER PUBLICATIONS

Orlova, V.S., et al., "Effect of Aerobic and Anaerobic Conditions on Chemical Composition and Enzyme Activity of Buds and Mother Cells of *Candida utilis,*" *Prikladnaya Biokhimiya i Mikrobiologiya.* 13(2) :260–264 (Mar.–Apr. 1977).

Vinogradov, B.D., et al., "Activation of L–Amino Acids by a Preparation of Aminoacyl–tRNA Synthetases From the Yeast *Candida utilis* IBFM–405," *Prikladnaya Biokhimiya i Mikrobiologiya,* 11(3) :378–381 (May–Jun. 1975).

Chalker, A.F., et al., "Analysis and Toxic Overexpression in *Escherichia coli* of a Staphylococcal Gene Encoding Isoleucyl–tRNA Synthetase," *Gene,* 141:103–108 (1994).

Jasin, M. and Schimmel, P., "Deletion of an Essential Gene in *Escherichia coli* by Site–Specific Recombination with Linear DNA Fragments," *J. Bacteriol.,* 159(2) :783–786 (1984).

Low, B., et al., "Isolation and Partial Characterization of Temperature–Sensitive *Escherichia coli* Mutants with Altered Leucyl– and Seryl–Transfer Ribonucleic Acid Synthetases," *J. Bacteriol.,* 108(2) :742–750 (1971).

Capobianco, John O., et al., "Anti–Candida Activity of Cispentacin: The Active Transport by Amino Acid Permeases and Possible Mechanisms of Action," *Biochemical and Biophysical Research Communications,* 190(3) : 1037–1044 (1993).

Ogawa, Kazuko, et al., "Anticodon Loop Structure of *Torulopsis utilis* tRNA$^{Val}$ and Valine Acceptance," *Journal of Advanced Science,* 5(2) :43–49 (1993).

Ohyama, Takashi, et al., "Studies on *T. utilis* tRNA$^{Tyr}$ Variants with Enzymatically Altered D–Loop Sequences: I. Deletion of the Conserved Sequence Gm–G and Its Effects on Aminoacylation and Conformation," *J. Biochem.,* 97(1) :29–36 (1985).

Racher, K.I., et al., "Expression and Characterization of a Recombinant Yeast Isoleucyl–tRNA Synthetase," *J. Biol. Chem.,* 266(26) :17158–17164 (1991).

Suzuki, Tsutomu, et al., "Characterization of Serine and Leucine tRNAs in an Asporogenic Yeast *Candida cylindracea* and Evolutionary Implications of Genes for tRNA$^{Ser}_{CAG}$ Responsible for Translation of a Non–Universal Genetic Code," *Nucleic Acids Research,* 22(2) :115–123 (1994).

Printout of a computer record of parts of a poster presented at Cap d'Agde, France, May 30–Jun. 4, 1993, 15th International tRNA Workshop, Société Francaise de Biochimie et Biologie Moléculaire.

Shiba, K., et al., "Human Cytoplasmic Isoleucyl–tRNA Synthetase: Selective Divergence of the Anticondon–Binding Domain and Acquisition of a New Structural Unit," *Proc. Natl. Acad. Sci. USA,* 91:7435–7439 (1994).

Shiba, K., et al., "Isolation of Higher Eukaryote Aminoacyl–tRNA Synthetase Genes by an Alignment–Guided Cross–Species PCR: Application to Human Isoleucine tRNA Synthetase," [From Programme and Abstracts, p. F.46], 15th International tRNA Workshop, Société Francaise de Biochimie et Biologie Moléculaire, Cap d'Agde, France, May 30–Jun. 4 (1993), Abstract No. 364.

Murasugi, A. and Hayashi, H., "Purification and Properties of Leucyl–tRNA Synthetase from *Candida Utilis,*" *Eur. J. Biochem.* 57:169–175 (1975).

Quinn, Cheryl L., et al., "Species–Specific Microhelix Aminoacylation by a Eukaryotic Pathogen tRNA Synthetase Dependent on a Single Base Pair," *Biochemistry,* 34(39) : 12489–12495 (1995).

Kaufman, C., "Cloning, Expression and Characterization of the Isoleucyl–tRNA Synthetase of *Candida albicans,*" Thesis, Naturwissenschaftliche Fakultät Universität Witten/Herdecke, 1995.

Ohama, Takeshi et al., "Non–Universal Decoding of the Leucine Codon CUG in Several Candida Species," *Nucleic Acids Research,* 21 (17) :4039–4045 (1993).

Leuker, Christoph E. and Ernst, Joachim F., "Toxicity of a Heterologous Leucyl–tRNA (anticodon CAG) in the Pathogen *Candida albicans*: In Vivo Evidence for Non–Standard Decoding of CUG Codons," *Mol. Gen. Genet.,* 245:212–217 (1994).

Houman, F., et al., "Cloning, Expression and Characterization of Isoleucyl–tRNA Synthetase from *Candida albicans,*" poster presented at Gordon Research Conference on Cellular and Molecular Mycology, Holderness School, Plymouth, New Hampshire, Jun. 16–17, 1996.

Frolova, L., et al., Data Submission, Human Tryptophanyl–tRNA Synthetase (WRS) mRNA, Homo sapiens, Accession No. M61715 (1991).

Garret, M., et al., Data Submission, Bovine Tryptophanyl–tRNA Ligase cDNA, Bos taurus, Accession Nos. M74074, J05334, X53918 (1991).

Lee, C.C., et al., Data Submission, Rabbit Eucaryotic Release Factor (eRF) mRNA, *Oryctolagus cuniculus,* Accession No. M33460 (1990).

Garret, M., Data Submission, *M. Musculus* (Clone S5) WRS mRNA for Tryptophan–tRNA Ligase, *Mus musculus,* Accession No. X69656 (1992).

Vandenbol, M., et al., Data Submission, *S. cerevisiae* Chromosome XV DNA (44 kb fragment), *Sacharomyces cerevisiae,* Accession No. Z48149 (1995).

Gentles, S., et al., Data Submission, *S. pombe* Chromosome I Cosmid c2F7, *Schizosaccharomyces pombe,* Accession No, Z50142 (1995).

John, Ted R., et al., "Identification and Expression of the *Saccharomyces cerevisiae* Cytoplasmic Tryptophanyl–tRNA Synthetase Gene," *Yeast,* 13:37–41 (1997).

Paley, Elena L., "A Mammalian Tryptophanyl–tRNA Synthetase Is Associated with Protein Kinase Activity," *Eur. J. Biochem.,* 244:780–788 (1997).

```
TAGAATATAAATCACTCCACATTTCATTAATGTCAGTTGAAGAAAAAGTATCACAGCTCAAAGTTACTGA
+----+----+----+----+----+----+----+----+----+----+----+----+----+----+ 70
ATCTTATATTTAGTGAGGTGTAAAGTAATTACAGTCAACTTCTTTTTCATAGTGTCGAGTTTCAATGACT
                         M  S  V  E  E  K  V  S  Q  L  K  V  T  E

GGAGTCAGAACAAAAAATCACTCCATGGGAAGTAGAAGGTGCCGTTGTAGAYGGGAAATCAATGGGGATT
+----+----+----+----+----+----+----+----+----+----+----+----+----+----+ 140
CCTCAGTCTTGTTTTTTAGTGAGGTACCCTTCATCTTCCACGGCAACATCTRCCCTTTAGTTACCCCTAA
 E  S  E  Q  K  I  T  P  W  E  V  E  G  A  V  V  D  G  K  S  M  G  I

GATTATGATAAATTAATTAGTCAATTCGGTACCAAACATATCACTGAGGAAACATTAGAAAGATTTAAAC
+----+----+----+----+----+----+----+----+----+----+----+----+----+----+ 210
CTAATACTATTTAATTAATCAGTTAAGCCATGGTTTGTATAGTGACTCCTTTGTAATCTTTCTAAATTTG
 D  Y  D  K  L  I  S  Q  F  G  T  K  H  I  T  E  E  T  L  E  R  F  K

AAGTTACTGGTGAAGAGCCTCATCCATTTTTGAAAAGAGGAGTATTTTTTTCACAAAGAGATTTAGATCG
+----+----+----+----+----+----+----+----+----+----+----+----+----+----+ 280
TTCAATGACCACTTCTCGGAGTAGGTAAAAACTTTTCTCCTCATAAAAAAAGTGTTTCTCTAAATCTAGC
 Q  V  T  G  E  E  P  H  P  F  L  K  R  G  V  F  F  S  Q  R  D  L  D  R

TATTTTAGATTTATATGAACACGGAGAACCATTCTTTTTATATACTGGAAGAGGTCCATCATCTGATTCA
+----+----+----+----+----+----+----+----+----+----+----+----+----+----+ 350
ATAAAATCTAAATATACTTGTGCCTCTTGGTAAGAAAAATATATGACCTTCTCCAGGTAGTAGACTAAGT
  I  L  D  L  Y  E  H  G  E  P  F  F  L  Y  T  G  R  G  P  S  S  D  S

ATGCATTTGGGTCATATGGTACCATTTATATTTACAAAATGGTTACAAGAAGTATTTGAYGTCCCATTAG
+----+----+----+----+----+----+----+----+----+----+----+----+----+----+ 420
TACGTAAACCCAGTATACCATGGTAAATATAAATGTTTTACCAATGTTCTTCATAAACTRCAGGGTAATC
 M  H  L  G  H  M  V  P  F  I  F  T  K  W  L  Q  E  V  F  D  V  P  L

TTATTGAATTAACTGATGATGAGAAATTTTTATTTAAACACCAATTAACTATTGATGATGTTAAAGGTTT
+----+----+----+----+----+----+----+----+----+----+----+----+----+----+ 490
AATAACTTAATTGACTACTACTCTTTAAAAATAAATTTGTGGTTAATTGATAACTACTACAATTTCCAAA
 V  I  E  L  T  D  D  E  K  F  L  F  K  H  Q  L  T  I  D  D  V  K  G  F

TGCCGCAGAAAATGCTAAAGATATAATTGCCGTTGGATTCAATCCGGAAAATACATTTATCTTTTCAGAT
+----+----+----+----+----+----+----+----+----+----+----+----+----+----+ 560
ACGGCGTCTTTTACGATTTCTATATTAACGGCAACCTAAGTTAGGCCTTTTATGTAAATAGAAAAGTCTA
  A  A  E  N  A  K  D  I  I  A  V  G  F  N  P  E  N  T  F  I  F  S  D

TTACAATATATGGGTGGAGCATTTTATGAAAACGTCGTTAGAACATCACGTCAAATCACTACTTCTACAG
+----+----+----+----+----+----+----+----+----+----+----+----+----+----+ 630
AATGTTATATACCCACCTCGTAAAATACTTTTGCAGCAATCTTGTAGTGCAGTTTAGTGATGAAGATGTC
 L  Q  Y  M  G  G  A  F  Y  E  N  V  V  R  T  S  R  Q  I  T  T  S  T

CTAAAGCAGTATTTGGATTCACTGATTCTGATTGTATTGGGAAAATACATTTTGCAAGTATTCAAATAGC
+----+----+----+----+----+----+----+----+----+----+----+----+----+----+ 700
GATTTCGTCATAAACCTAAGTGACTAAGACTAACATAACCCTTTTATGTAAAACGTTCATAAGTTTATCG
 A  K  A  V  F  G  F  T  D  S  D  C  I  G  K  I  H  F  A  S  I  Q  I  A
```

FIG. 1A

```
AACTGCATTCCCATCATCATTCCCCGATGTATTAGGATTACCACCAAAGACCCCTTGTTTAATTCCTTGT
                                                                         770
TTGACGTAAGGGTAGTAGTAAGGGGCTACATAATCCTAATGGTGGTTTCTGGGGAACAAATTAAGGAACA
  T  A  F  P  S  S  F  P  D  V  L  G  L  P  P  K  T  P  C  L  I  P  C

GCCATAGATCAAGATCCTTATTTTAGAGTTTGTAGAGATGTTGCCGATAAATTAAGATTTACCAAACCAG
                                                                         840
CGGTATCTAGTTCTAGGAATAAAATCTCAAACATCTCTACAACGGCTATTTAATTCTAAATGGTTTGGTC
  A  I  D  Q  D  P  Y  F  R  V  C  R  D  V  A  D  K  L  R  F  T  K  P

CATTAATTCATGCTAAATTTTTCCCAGCTTTACAAGGGGCATCGACAAAAATGTCAGCTTCTGATACTAC
                                                                         910
GTAATTAAGTACGATTTAAAAAGGGTCGAAATGTTCCCCGTAGCTGTTTTTACAGTCGAAGACTATGATG
  A  L  I  H  A  K  F  F  P  A  L  Q  G  A  S  T  K  M  S  A  S  D  T  T

AACTTCGATTTTCATGGGTGATACAGCAAAACAAATTCAGAAAAAAATTAATAAATATGCATTTTCCGGT
                                                                         980
TTGAAGCTAAAAGTACCCACTATGTCGTTTTGTTTAAGTCTTTTTTTAATTATTTATACGTAAAAGGCCA
  T  S  I  F  M  G  D  T  A  K  Q  I  Q  K  K  I  N  K  Y  A  F  S  G

GGTAGAGCCACTGCTGAAGAACATCGRGAATTAGGAGGTAACCCAGAAGTAGATGTTGCATTCCAATATT
                                                                         1050
CCATCTCGGTGACGACTTCTTGTAGCYCTTAATCCTCCATTGGGTCTTCATCTACAACGTAAGGTTATAA
   G  R  A  T  A  E  E  H  R  E  L  G  G  N  P  E  V  D  V  A  F  Q  Y

TATCATTTTTCAGTTATGATGATGAAAAATTGGCACAATTAGAACAAGGTTATAGAAAGGGAGAAATATT
                                                                         1120
ATAGTAAAAAGTCAATACTACTACTTTTTAACCGTGTTAATCTTGTTCCAATATCTTTCCCTCTTTATAA
   L  S  F  F  S  Y  D  D  E  K  L  A  Q  L  E  Q  G  Y  R  K  G  E  I  L

ATCAGGAGAAATGAAAAAAGAATGTATTACAGTTTTACAAGAATTTGTATCTGCTTATCAAGAAAGAAGA
                                                                         1190
TAGTCCTCTTTACTTTTTTCTTACATAATGTCAAAATGTTCTTAAACATAGACGAATAGTTCTTTCTTCT
    S  G  E  M  K  K  E  C  I  T  V  L  Q  E  F  V  S  A  Y  Q  E  R  R

AGTAAAGTTGAYGACCAAGTTGTTGAAAAATTCATGAAACCACATAAATTGGTGTTTGGTAATAAGGAAA
                                                                         1260
TCATTTCAACTRCTGGTTCAACAACTTTTTAAGTACTTTGGTGTATTTAACCACAAACCATTATTCCTTT
    S  K  V  D  D  Q  V  V  E  K  F  M  K  P  H  K  L  V  F  G  N  K  E

GAAAAGTTCCTGCCAAACAAAGAGAAAAGAAAGCCAAAAAGTAAATCAGGCTTGAATACAATGGAGATAC
                                                                         1330
CTTTTCAAGGACGGTTTGTTTCTCTTTTCTTTCGGTTTTTCATTTAGTCCGAACTTATGTTACCTCTATG
   R  K  V  P  A  K  Q  R  E  K  K  A  K  K

ATATTTATATAGTAGAGTAATCTATAGATATTAATT
                                        1366
TATAAATATATCATCTCATTAGATATCTATAATTAA
```

FIG. 1B

CANDIDA CYTOPLASMIC TRYPTOPHANYL-TRNA SYNTHETASE PROTEINS, NUCLEIC ACIDS AND STRAINS COMPRISING SAME

BACKGROUND OF THE INVENTION

*Candida albicans* is an opportunistic pathogen and the most common fungus causing systemic infections in man including both bloodstream infections in hospitalized immunocompromised patients and vaginal infections (for review, see: Mandell, G. L.; Bennett, J. E.; and Dolin, R. (Eds), *Principles and Practice of Infectious Disease*, 4th ed., Churchill Livingston: New York, 1995; Vol 2, Chapter 237). The increasing use of immunosuppressive therapy for malignancy and transplantation, the increase in intensive care patients receiving broad spectrum antibiotic therapy, and the AIDS epidemic have greatly increased the number of patients susceptible to opportunistic infections caused by *C. albicans*. In particular, infections due to Candida increased by almost 500% over the decade of the 1980s and continue to rise in the 1990s, becoming the fourth most common blood-stream pathogen (see: Pfaller, M. A. *Journal of Hospital Infection* 30 suppl. 329–38 1995). It has been reported that 90% of AIDS patients have some type of Candida infection. *C. albicans* can invade the kidneys, heart, liver, lungs, spleen, brain and eyes. These infections are difficult to detect and can lead to death.

A limited number of antifungal agents are available for the treatment for *C. albicans* infections. Amphotericin B, the mainstay of antifungal therapy, has limited clinical utility in treating Candida infection due to its associated toxicities and requirement for intravenous administration. Flucytosine too is limited due to its bone marrow toxicity and to the appearance of resistance. The azole antifungal agents have become the first choice of therapy for Candida infection and fluconazole is the most frequent drug prescribed in the 1990's. However, reports of resistance to these azole antifungals have appeared in recent years (see: Dupont, B. *Current Opinion in Infectious Diseases* 8, 424–427 1995). Because of the development of resistance to antifungals and adverse side-effects of current therapies for Candida infection, there is continuing need for new drug targets and new antibiotics.

SUMMARY OF THE INVENTION

The invention relates to isolated and/or recombinant nucleic acids which encode cytoplasmic tryptophanyl-tRNA synthetases of Candida origin. The invention also relates to recombinant DNA constructs and vectors containing DNA having a sequence which encodes a cytoplasmic tryptophanyl-tRNA synthetase of Candida origin or portions of the enzyme. These nucleic acids and constructs can be used to produce recombinant cytoplasmic tryptophanyl-tRNA synthetases of Candida origin.

A further embodiment of the invention is antisense nucleic acid which can hybridize to the nucleic acid which encodes a cytoplasmic tryptophanyl-tRNA synthetase of Candida. In cells, antisense nucleic acid can inhibit the function of an RNA which encodes a cytoplasmic tryptophanyl-tRNA synthetase of Candida.

The invention also relates to proteins or polypeptides, including fusion proteins, referred to herein as isolated and/or recombinant Candida cytoplasmic tryptophanyl-tRNA synthetases. These proteins are useful in the synthesis of peptides and related products; in assays to identify inhibitors of cytoplasmic tryptophanyl-tRNA synthetase function (including inhibitors having antimicrobial activity); in biochemical separations of tryptophan; and in quantitations of tryptophan and ATP. Antibodies which bind to cytoplasmic tryptophanyl-tRNA synthetases can be made and can be used in the purification and study of these enzymes.

Recombinant Candida cytoplasmic tryptophanyl-tRNA synthetases can be produced in host cells using cells and methods described herein. Tester strains, which are cells engineered to rely on the function of the tRNA synthetase encoded by an introduced cloned gene, are also an embodiment of the invention. Tester strains can be used to test the effectiveness and/or specificity of drug candidates in the inhibition of the essential tRNA synthetase enzyme encoded by the introduced cloned gene. In this way, potential inhibitors of the enzyme can be screened for antimicrobial or antibiotic effects, without requiring the culture of pathogenic strains of Candida, such as *Candida albicans*.

BRIEF DESCRIPTION OF THE DRAWINGS

FIGS. 1A–1B is an illustration of the 1366-basepair nucleotide sequence determined for the cytoplasmic tryptophanyl-tRNA synthetase gene of *C. albicans* (SEQ ID NO: 25) and the amino acid sequence of the encoded protein as translated by the universal genetic code (SEQ ID NO:26), starting from the initiator methionine at base 30. Standard one-letter amino acid codes are used.

DETAILED DESCRIPTION OF THE INVENTION

Figure 2:
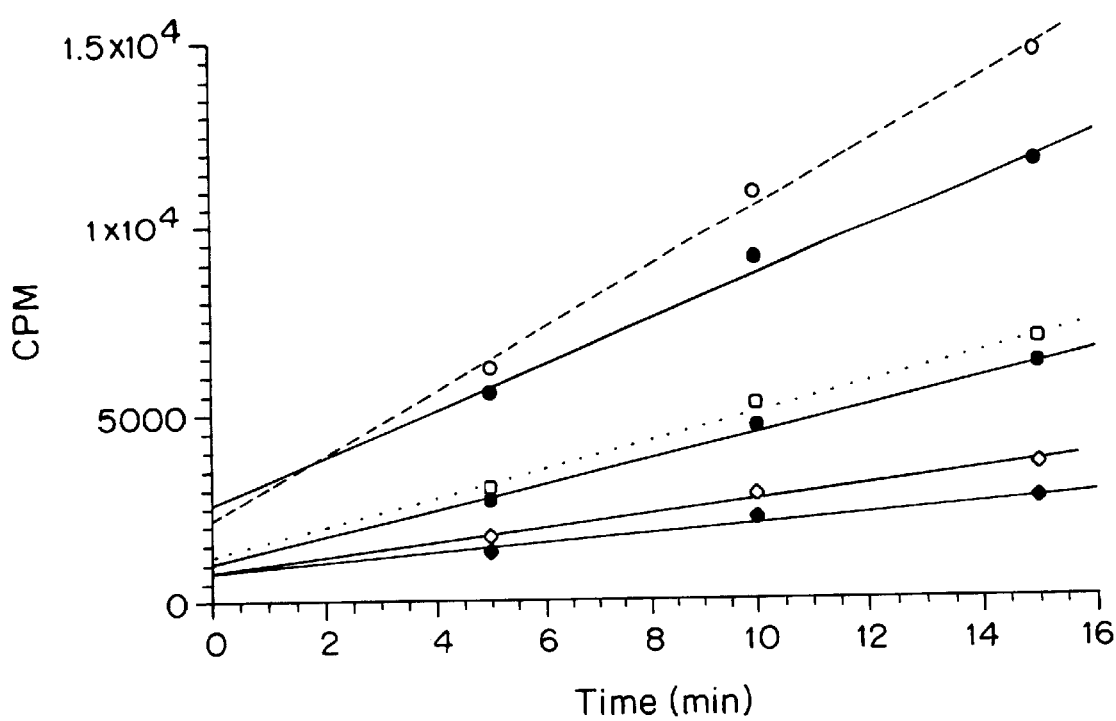
FIG. 2 is a graph illustrating the aminoacylation activity (cpm, counts per minute of [$^3$H]Trp-tRNA) over time (minutes) of the purified TrpRS expressed from pC$^3$822 as described in Example 6.

The aminoacyl-tRNA synthetases are enzymes with the common general function of catalyzing the following reaction:

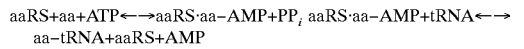

(aaRS=aminoacyl-tRNA synthetase; aa=amino acid; ATP=adenosine 5'-triphospate; AMP=adenosine 5'-monophosphate; PP$_i$=inorganic pyrophosphate) The second (aminoacylation) step is often referred to as "charging" the tRNA.

Some enzymes studied to date (e.g., GluRS) require binding of tRNA for catalysis. Thus, the overall reaction can be summarized:

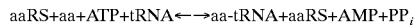

Generally, with the exception of some gram-positive organisms, bacteria have up to 20 aminoacyl-tRNA synthetases, each specific for a different amino acid. Eucaryotic organisms also typically encode 20 cytoplasmic aaRSs, one specific for each amino acid. In addition, eucaryotic organisms generally encode a separate set of mitochondrial aaRSs. In the yeast *Saccharomyces cerevisiae*, the cytoplasmic and mitochondrial enzymes are usually encoded by separate nuclear genes, with several exceptions (e.g., histidyl- and valyl-tRNA synthetases (Natsoulis, G., et al., *Cell* 46:235–243 (1986); Chatton, B., et al., *J. Biol. Chem.* 263:52–57 (1988)). Each aminoacyl-tRNA synthetase enzyme recognizes and reacts with a specific amino acid and with one or more tRNAs that recognize the codons specific for that amino acid (cognate tRNAs). An exception has been found in some gram positive organisms, such as *B. subtilis*, in which no glutaminyl-tRNA synthetase activity has been detected. In these organisms, both tRNA$^{Glu}$ and tRNA$^{Gln}$ are aminoacylated with glutamate. *B. subtilis* GluRS has been purified to homogeneity, and has been demonstrated to aminoacylate tRNA$^{Glu}$ and tRNA$^{Gln}$ with glutamate (Proulx, M. and J. Lapointe, *Meth. Enzymol.*, 113:50–54 (1985); Lapointe, J. et al. *J. Bacteriol.*, 165:(1):88–93 (1986)). In some gram positive organisms, including *B. Subtilis*, the glutamyl-tRNA$^{Gln}$ is converted into glutaminyl-tRNA$^{Gln}$ by an amidotransferase in the presence of an amide donor and ATP. The specificity of the aaRS for the amino acid is determined by protein-amino acid interactions, and the specificity of the aaRS for the tRNA is determined by protein-RNA interactions, using different sites on the aaRS and tRNA molecules.

The tRNA synthetases can be subdivided into two groups of enzymes, class I and class II, based on short regions of sequence homology as well as distinct active site core tertiary structures (Eriani, G., et al., *Nature* 347:203–206 (1990); Moras, D., *Trends Biochem. Sci.* 17:159–164 (1992); Burbaum, J. J. and Schimmel, P., *J. Biol Chem.* 266(26) :16965–16968 (1991)). For example, the small dimeric tryptophanyl-tRNA synthetase of *E. coli* has been classified as a class I synthetase. This enzyme contains the signature peptide sequences, HIGH and KMSKS, that are part of the nucleotide binding fold present in all class I synthetases.

Nucleic Acids, Constructs and Vectors

The present invention relates to isolated and/or recombinant (including, e.g., essentially pure) nucleic acids having sequences which encode a Candida cytoplasmic tryptophanyl-tRNA synthetase, or a portion of a Candida cytoplasmic tryptophanyl-tRNA synthetase. In one embodiment, the nucleic acid or portion thereof encodes a protein or polypeptide having at least one function that is characteristic of a Candida cytoplasmic tryptophanyl-tRNA synthetase, such as a catalytic activity (e.g., catalysis of tryptophanyl-adenylate or PP$_i$ formation, catalysis of aminoacylation of a tRNA with tryptophan), and/or binding function (e.g., tRNA-, tryptophan- or ATP-binding), and/or antigenic function (e.g., binding of antibodies that also bind to a naturally occurring Candida cytoplasmic TrpRS), and/or oligomerization function. Oligomerization activity is the ability of a protein subunit or protein fragment to bind together with one or more other protein subunits or protein fragments, thus altering the quaternary structure of the resulting complex. For example, "adhesive" fragments with oligomerization activity can bind to another fragment with no catalytic activity of its own to restore or partially restore enzymatic activity (Jasin, M., et al., U.S. Pat. No. 4,952, 501). The present invention also relates more specifically to isolated and/or recombinant nucleic acids or a portion thereof having sequences which encode a cytoplasmic tryptophanyl-tRNA synthetase of *Candida albicans* origin, or a portion thereof.

The invention further relates to isolated and/or recombinant nucleic acids that are characterized by (1) the ability to hybridize to (a) a nucleic acid having the sequence of FIGS. 1A–1B (SEQ ID NO:25) or portions thereof (e.g., a portion comprising the open reading frame); or (2) the ability to encode a polypeptide having the amino acid sequence of a Candida cytoplasmic tryptophanyl-tRNA synthetase (e.g., SEQ ID NO:25) or portions thereof, or functional equivalents thereof (e.g., a polypeptide which aminoacylates the isoaccepting cognate tRNAs (such as tRNA$^{Trp}$ of *C. albicans*) with tryptophan); or (3) both characteristics. A nucleic acid which hybridizes to a nucleic acid encoding a Candida cytoplasmic TrpRS such as SEQ ID NO:25, can be double- or single-stranded. Hybridization to DNA such as DNA having the sequence SEQ ID NO:25 includes hybridization to the coding strand or its complementary strand. In one embodiment, the percent nucleotide sequence identity between the open reading frame of an isolated and/or recombinant nucleic acid encoding a Candida cytoplasmic tryptophanyl-tRNA synthetase, such as that depicted in FIGS. 1A–1B (SEQ ID NO:25), and nucleic acids encoding functional equivalents of the tryptophanyl-tRNA synthetase, is at least about 65%, preferably at least about 75%, more preferably at least about 80%, even more preferably at least about 90%, and still more preferably, at least about 95% . Preferably, the percent amino acid sequence similarity between a Candida cytoplasmic tryptophanyl-tRNA synthetase, such as the polypeptide encoded by SEQ ID NO:25, and functional equivalents thereof is at least about 75%. More preferably, the percent amino acid sequence similarity between a Candida cytoplasmic tryptophanyl-tRNA synthetase and its functional equivalents is at least about 80%, and still more preferably, at least about 90%. In a preferred embodiment, nucleic acids of the present invention are at least about 8, 12, 18, 25, 40 or 50 nucleotides in length. Preferably, the nucleic acids can hybridize specifically to the nucleic acid illustrated in FIGS. 1A–1B (SEQ ID NO:25) or the open reading frame thereof.

Isolated and/or recombinant nucleic acids meeting these criteria comprise nucleic acids having sequences identical to sequences of naturally occurring Candida cytoplasmic TrpRS genes, including allelic variants, and portions thereof, or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues. In one embodiment, the isolated and/or recombinant nucleic acid encodes a cytoplasmic tryptophanyl-tRNA synthetase of a pathogenic species of Candida, including *C. albicans, C. utilis, C. pseudotropicalis, C. stellatoidea, C. guilliermondi, C. glabrata, C. krusei, C. parapsilosis,* and *C. tropicalis*. In another embodiment, the isolated and/or recombinant nucleic acid encodes a cytoplasmic tryptophanyl-tRNA synthetase of a Candida species other than *C. utilis*. Preferred embodiments of isolated and/or recombinant nucleic acids are those encoding cytoplasmic tryptophanyl-tRNA synthetases of *C. albicans*.

Such nucleic acids, including DNA or RNA, can be detected and isolated by hybridization (e.g., under high stringency conditions or moderate stringency conditions). "Stringency conditions" for hybridization is a term of art which refers to the conditions of temperature and buffer concentration which permit hybridization of a particular nucleic acid to another nucleic acid in which the first nucleic acid may be perfectly complementary to the second, or the first and second may share only some degree of complementarity. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology*, for example (Ausubel, F. M., et al., Eds., Vol. 1, containing supplements up through Supplement 37, 1997), the teachings of which are hereby incorporated by reference. The exact conditions which determine the stringency of hybridization depend on factors such as length of the nucleic acids, base composition, percent and distribution of mismatch between hybridizing sequences, temperature, ionic strength, concentration of destabilizing agents such as formamide, and the frequency of occurrence of subsets of the hybridizing sequence within other non-identical sequences. Thus, high or moderate stringency conditions can be determined empirically.

For example, if a set of hybridization conditions is used which is determined to allow hybridization between nucleic acids which are too dissimilar in sequence for the purposes of an experiment, then the hybridization conditions can be altered in subsequent experiments to a higher stringency to achieve selectivity to the desired level of sequence similarity. Higher stringency conditions can be achieved, for example, by raising the temperature of the hybridization and/or post-hybridization washes; and/or by decreasing the ionic strength (usually, the SSC concentration) of the hybridization buffer and/or post-hybridization washes; and/or by addition of certain reagents (e.g., formamide).

By varying hybridization conditions from a level of stringency at which no hybridization occurs to a level at which hybridization is first observed, conditions which will allow a given sequence to hybridize with the most similar sequences in the sample can also be determined.

Exemplary conditions are described in Krause, M. H. and Aaronson, A. S.; *Methods in Enzymology*, 200:546–556 (1991). See also page 2.10.11 in *Current protocols in Molecular Biology* (supra), which describes how to determine washing conditions. Washing is the step in which conditions are usually set so as to determine a minimum level of complementarity of the hybrids and to eliminate free non-hybridized radioactive probe as well as background and non-specific weak interaction. Generally, starting from the lowest temperature at which only homologous hybridization occurs, each degree Celsius by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

Isolated and/or recombinant nucleic acids that are characterized by their ability to hybridize to a nucleic acid encoding a Candida cytoplasmic tryptophanyl-tRNA synthetase, such as the nucleic acid depicted in SEQ ID NO:25, or a portion therof (e.g. under high or moderate stringency conditions), may further encode a protein or polypeptide having at least one function that is characteristic of a Candida cytoplasmic tryptophanyl-tRNA synthetase, such as a catalytic activity (e.g., tryptophanyl-adenylate or $PP_i$ formation, aminoacylation of a tRNA with tryptophan), binding function (e.g., tRNA-, tryptophan-, or ATP-binding), antigenic function (e.g., binding of antibodies that also bind to a naturally occurring Candida cytoplasmic TrpRS), and/or oligomerization function.

The catalytic or binding function of a protein or polypeptide encoded by a nucleic acid of the present invention can be detected by standard enzymatic assays for activity or binding (e.g., assays which monitor aminoacyl-adenylate formation, aminoacylation of tRNA with tryptophan). Functions that are characteristic of a cytoplasmic tryptophanyl-tRNA synthetase can also be assessed by in vivo complementation activity or other suitable methods. Enzymatic assays, complementation tests, or other suitable methods can also be used in procedures for the identification and/or isolation of nucleic acids which encode a polypeptide such as a polypeptide of the amino acid sequence SEQ ID NO:26, or functional equivalents of these polypeptides. The antigenic properties of proteins or polypeptides encoded by nucleic acids of the present invention can be determined by immunological methods employing antibodies that bind to a Candida cytoplasmic tryptophanyl-tRNA synthetase, such as immunoblot, immunoprecipitation and radioimmunoassay.

The identification of additional Candida cytoplasmic TrpRS genes can also be accomplished by an extension of the methods used to isolate *Candida albicans* cytoplasmic TrpRS-specific fragments as explained in Examples 1–3. For example, pairs of degenerate oligonucleotides that were successfully used in a PCR reaction to identify the *C. albicans* cytoplasmic TrpRS gene can be used in PCR reactions using the reaction conditions described below or other suitable conditions. Since these primer pairs, which were created based upon DNA sequence information of non-Candida species, were able to amplify a *C. albicans* PCR product, it is reasonable to expect that they can amplify a PCR product from other related Candida species. The same degenerate primer pairs that were used in PCR reactions to isolate *C. albicans* cytoplasmic TrpRS-specific fragments can be used with other Candida species (e.g., genomic DNA, a cloned library). Primer design can also take into account the sequence of *C. albicans* TrpRS and its nucleotide sequence. Once a fragment of a Candida cytoplasmic TrpRS is generated by PCR, it can be sequenced. To determine if the DNA sequence of the PCR product encodes an TrpRS, the sequence of the product can be compared to other DNA sequences. The entire gene sequence (including the 5' and 3' ends) can then be identified using suitable methods, such as semi-specific PCR.

A cytoplasmic tryptophanyl-tRNA synthetase gene or portion thereof is producible by methods described herein or other suitable methods. For example, primers (e.g., a pair of primers or nested primers) can be designed which comprise a sequence which is complementary or substantially complementary to a portion of the gene encoding *C. albicans* cytoplasmic TrpRS. Primers can contain portions which are complementary to other sequences as appropriate, such as restriction recognition sequences, template sequences (e.g., vector sequences flanking the inserts in a gene library) or other sequences. For instance, primers complementary to the 5'- and 3'- ends of the coding sequence and or flanking regions shown in FIGS. 1A–1B (SEQ ID NO:25) can be designed. Such primers can be used in a polymerase chain reaction with a suitable nucleic acid template (e.g., a construct described herein, a library or another suitable nucleic acid) to obtain a Candida cytoplasmic TrpRS gene or portion thereof.

Nucleic acids of the present invention can be used in the production of proteins or polypeptides. For example, DNA containing all or part of the coding sequence for a Candida cytoplasmic tryptophanyl-tRNA synthetase, or DNA which hybridizes to DNA having the sequence SEQ ID NO:25, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction into the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). Thus, as used herein, a nucleic acid which encodes a portion of a tryptophanyl-tRNA synthetase can also refer to one of two or more distinct subunits of said tRNA synthetase.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to, and can hybridize with, a target nucleic acid, wherein the target nucleic acid can hybridize to a nucleic acid having the sequence of the complement of the top strand shown in FIGS. 1A–1B (SEQ ID NO:25). For example, antisense nucleic acid can be complementary to a target nucleic acid having the sequence shown as the top strand of the open reading frame in FIGS. 1A–1B (SEQ ID NO:25), or to a portion thereof sufficient to allow hybridization. In another embodiment, the antisense nucleic acid is wholly or partially complementary to and can hybridize with a target nucleic acid which encodes a Candida cytoplasmic tryptophanyl-tRNA synthetase.

C. albicans is the most important human pathogen among Candida species. Because advances in the understanding and treatment of C. albicans infection would be of benefit, it was the species selected for most of the experimental work described herein. As described in the Exemplification, PCR fragments of C. albicans cytoplasmic TrpRS gene were isolated, cloned and used to isolate a C. albicans TrpRs gene.

The isolated C. albicans gene is representative of a broader class of Candida cytoplasmic tryptophanyl-tRNA synthetase genes derived from various species of Candida. These additional genes can also be used to express Candida cytoplasmic tryptophanyl-tRNA synthetases, with utilities corresponding to those described herein, and can be used in the production of host cells and tester strains comprising recombinant Candida cytoplasmic tryptophanyl-tRNA synthetase genes using methods described herein. The approaches described herein, including, but not limited to, the approaches to isolate and manipulate the cytoplasmic tryptophanyl-tRNA synthetase gene of C. albicans, to construct vectors and host strains, and to produce and use the protein, to produce antibodies, etc., can be applied to other members of the genus Candida, including, but not limited to, pathogenic species such as C. pseudotropicalis, C. utilis, C. stellatoidea, C. guilliermondi, C. glabrata, C. krusei, C. parapsilosis, and C. tropicalis. For example, the cytoplasmic tryptophanyl-tRNA synthetase gene described here or sufficient portions thereof, whether isolated and/or recombinant or synthetic, including fragments produced by PCR, can be used to detect and/or recover homologous genes of other Candida species (e.g., as probes for hybridization, or primers for PCR or other suitable techniques).

Proteins

The invention also relates to proteins or polypeptides encoded by nucleic acids of the present invention. The proteins and polypeptides of the present invention can be isolated and/or recombinant. Proteins or polypeptides referred to herein as "recombinant" are proteins or polypeptides produced by the expression of recombinant nucleic acids. Proteins or polypeptides referred to herein as "isolated" are proteins or polypeptides purified to a state beyond that in which they exist in cells, and include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated.

In one embodiment, proteins or polypeptides are isolated to a state at least about 65% pure; more preferably at least about 75% pure; still more preferably at least about 85% pure; and even more preferably at least about 90% pure, as determined by Coomassie blue staining of proteins on SDS-polyacrylamide gels.

In a preferred embodiment, the protein or portion thereof has at least one function that is characteristic of a Candida cytoplasmic tryptophanyl-tRNA synthetase, such as catalytic activity (e.g., catalysis of aminoacyl-adenylate or $PP_i$ formation, catalysis of aminoacylation of tRNA with tryptophan), binding function (e.g., tRNA-, amino acid-, or ATP-binding), antigenic function (e.g., binding of antibodies that also bind to a naturally occurring Candida cytoplasmic tryptophanyl-tRNA synthetase), and/or oligomerization activity. As such, these proteins are referred to as cytoplasmic tryptophanyl-tRNA synthetases of Candida origin or Candida cytoplasmic tryptophanyl-tRNA synthetases, and include, for example, naturally occurring Candida cytoplasmic tryptophanyl-tRNA synthetases (including allelic variants), variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

In a preferred embodiment, an isolated and/or recombinant Candida cytoplasmic tryptophanyl-tRNA synthetase or functional portion thereof is active, i.e., has a catalytic activity, such as catalysis of formation of aminoacyl-adenylate or $PP_i$ and/or catalysis of aminoacylation of an isoaccepting tRNA.

In one preferred embodiment of isolated and/or recombinant protein, the cytoplasmic tryptophanyl-tRNA synthetase is from C. albicans. Other preferred embodiments are isolated and/or recombinant cytoplasmic tryptophanyl-tRNA synthetases of pathogenic Candida species, including Candida species other than C. utilis, particularly C. pseudotropicalis, C. stellatoidea, C. guilliermondi, C. glabrata, C. krusei, C. parapsilosis, and C. tropicalis.

In a particularly preferred embodiment, like naturally occurring Candida cytoplasmic tryptophanyl-tRNA synthetase, isolated and/or recombinant Candida cytoplasmic tryptophanyl-tRNA synthetases of the present invention aminoacylate the isoaccepting cognate tRNAs of the Candida organism with tryptophan in a two-step reaction. For example, an isolated and/or recombinant *C. albicans* cytoplasmic tryptophanyl-tRNA synthetase is able to aminoacylate each of the isoaccepting species of cognate tRNA$^{Trp}$ of *C. albicans* with tryptophan. In the first step, the Candida cytoplasmic tryptophanyl-tRNA synthetase catalyzes the covalent linkage of tryptophan to ATP to form an adenylate complex (tryptophanyl-adenylate) with the release of pyrophosphate, and, in a second step, catalyzes the covalent linkage of tryptophan to a specific tRNA recognized by the enzyme, releasing AMP.

It should be noted that certain species of Candida, including *C. albicans, C. parapsilosis, C. zeylanoldes, C. rugosa, C. melibiosica* and *C. cylindracea*, are known to use a variation of the "universal" genetic code which appears in genetics textbooks and treatises (for example, see pages 104–105 in Lewin, B., *Genes*, 3rd edition, John Wiley and Sons, New York, 1987; Ohama, T. et al., *Nucleic Acids Res.* 21:4039–4045 (1993)). It is known that in these species of Candida, the codon CUG, which codes for leucine in the universal genetic code, is decoded as serine by a non-universal genetic code of these species of Candida. It is possible that in these species of Candida, other codons may also determine a different amino acid from that determined by the universal code. Thus, the expression of a gene, such as a cytoplasmic TrpRS gene, in certain species of Candida, can result in a protein having a different amino acid sequence from the amino acid sequence that would result from the expression of the same gene in an organism using the universal genetic code. Other species of Candida which decode CUG as leucine include *C. magnoliae, C. azyma, C. diversa*, and *C. rugopelliculosa* (Ohama et al.).

The invention further relates to fusion proteins, comprising a Candida cytoplasmic tryptophanyl-tRNA synthetase (as described above) as a first moiety, linked to second moiety not occurring in the Candida cytoplasmic TrpRS as found in nature. Thus, the second moiety can be an amino acid or polypeptide. The first moiety can be in an N-terminal location, C-terminal location or internal to the fusion protein. In one embodiment, the fusion protein comprises a *C. albicans* cytoplasmic tryptophanyl-tRNA synthetase as the first moiety, and a second moiety comprising a linker sequence and affinity ligand.

Fusion proteins can be produced by a variety of methods. For example, a fusion protein can be produced by the insertion of a cytoplasmic TrpRS gene or portion thereof into a suitable expression vector, such as Bluescript SK +/− (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., *Current Protocols in Molecular Biology* (Ausubel, F. M., et al., Eds., Vol. 2, Suppl. 26, pp. 16.4.1–16.7.8 (1991)).

The invention also relates to isolated and/or recombinant portions or fragments of a cytoplasmic tryptophanyl-tRNA synthetase of Candida origin. Portions of the enzyme can be made which have full or partial function on their own, or which when mixed together (though fully, partially, or nonfunctional alone), spontaneously assemble with one or more other polypeptides to reconstitute a functional protein having at least one function characteristic of a Candida cytoplasmic tryptophanyl-tRNA synthetase. (See, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; Burbaum, J. and Schimmel, P., *Biochemistry* 30(2): 319–324 (1991), describing non-overlapping segments of *E. coli* MetRS that can fold together to reconstitute an active enzyme capable of recognizing and charging tRNA in vitro and in vivo; Jasin, M., et al., (U.S. Pat. No. 4,952,501) describing deletion studies of *E. coli* alanyl-tRNA synthetase which showed that large portions of the protein were unnecessary for specific amino acylation activity). Based on this type of analysis, portions of a Candida cytoplasmic TrpRS can be made which have at least one function that is characteristic of a Candida cytoplasmic tryptophanyl-tRNA synthetase, such as catalytic function, binding function, antigenic function and/or oligomerization function. Studies on the structure and function of the aaRSs provide the basis for being able to divide the Candida aaRS enzymes into functional domains (Schimmel, P., *Current Biology* 1:811–816 (1991)).

The sequences and structures of the catalytic domains of several tRNA synthetases which have been purified and studied have led to the identification of two distinct classes designated class I and class II (Schimmel, P., *Ann. Rev. Biochem.* 56:125–158 (1987); Webster, T. A., et al., *Science* 226:1315–1317 (1984); Eriani, G., et al , *Nature* 347:203–206 (1990) and Cusack, S., et al., *Nature* 347:249–255 (1990)). Class I enzymes have a well-conserved N-terminal nucleotide binding fold responsible for amino acid binding, aminoacyl-adenylate formation, and tRNA acceptor helix docking. The N-terminal Rossman nucleotide binding fold is comprised of alternating β-strands and α-helices and comprises conserved motifs such as the HIGH tetrapeptide located in the first half of the Rossman fold and the KMSKS pentapeptide located in the second half of the Rossman fold. These elements are landmarks of class I synthetases. The C-terminal domain is rich in α-helices and contains residues needed for interactions with the parts of the tRNA distal to the amino acid attachment site (Shepard, A., et al., *Proc. Natl. Acad. Sci. U.S.A.* 89:9964–9968 (1992); Hou, Y.-M., et al., *Proc. Natl. Acad. Sci. U.S.A.* 88:976–980 (1991)). In some tRNA synthetases, this second domain interacts directly with the anticodon (Rould, M. A., et al., *Science* 246:1135–1142 (1989) and Cavarelli, J., et al., *Nature* 362:181–184 (1993)), while in other enzymes there is no contact made between the second domain and the anticodon (Biou, V., et al., *Science* 263:1404–1410 (1994)). To a first approximation, the two domains in class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

Consideration of this information, along with the remaining teachings of the specification, allows the construction of *C. albicans* cytoplasmic tryptophanyl-tRNA synthetase derivatives which possess at least one function that is characteristic of a Candida cytoplasmic tryptophanyl-tRNA synthetase.

Method of Producing Recombinant Cytoplasmic TrpRSs

Another aspect of the invention relates to a method of producing a Candida cytoplasmic tryptophanyl-tRNA synthetase or a portion thereof, and to expression systems and host cells containing a vector appropriate for expression of the Candida cytoplasmic tryptophanyl-tRNA synthetase.

Cells that express a recombinant cytoplasmic tryptophanyl-tRNA synthetase or a portion thereof can be made and maintained in culture under conditions suitable for expression to produce protein for isolation. These cells can be procaryotic or eucaryotic. Examples of procaryotic cells that can be used to express Candida cytoplasmic tryptophanyl-tRNA synthetases include *Escherichia coli* (e.g., BL21, BL22, JM109), *Bacillus subtilis* and other bacteria. Examples of eucaryotic cells that can be used to express the cytoplasmic tryptophanyl-tRNA synthetases include yeasts such as *Saccharomyces cerevisiae, S. pombe, Pichia pastoris,* and other lower eucaryotic cells, as well as cells of higher eucaryotes, such as those from insects and mammals. (See, e.g., Ausubel, F. M. et al., Eds. *Current Protocols in Molecular Biology,* Greene Publishing Associates and John Wiley & Sons Inc., (1993)).

In one embodiment, host cells that produce a recombinant Candida cytoplasmic TrpRS protein or portion thereof for isolation and purification can be made as follows. A gene encoding a cytoplasmic TrpRS can be inserted into a nucleic acid vector, e.g., a DNA vector, such as a plasmid, virus or other suitable replicon, which can be present in a single copy or multiple copies, or the gene can be integrated in a host cell chromosome. A suitable replicon or integrated gene can contain all or part of the coding sequence for Candida cytoplasmic tryptophanyl-tRNA synthetase or variant, operably linked to one or more expression control sequences whereby the coding sequence is under the control of transcription signals and linked to appropriate translation signals to permit translation of the cytoplasmic TrpRS. A nucleic acid or vectors can be introduced into cells by a method appropriate to the type of host cells (e.g., transformation, electroporation, transfection, infection). For expression from the cytoplasmic TrpRS gene, the host cells can be maintained under appropriate conditions, e.g., in the presence of inducer, normal growth conditions, etc.).

For example, Candida cytoplasmic tryptophanyl-tRNA synthetase can be produced by integrating a gene encoding the *C. albicans* cytoplasmic TrpRS into the genome of a virus that enters the host cells. By infection of the host cells, the components of a system which permits the transcription and translation of the Candida cytoplasmic TrpRS gene are present in the host cells. Alternatively, an RNA polymerase gene, inducer, or other component required to complete such a gene expression system may be introduced into the host cells already containing the Candida cytoplasmic TrpRS gene, for example, by means of a virus that enters the host cells and contains the required component. The Candida cytoplasmic TrpRS gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Antibodies

The invention further relates to antibodies that bind to an isolated and/or recombinant Candida cytoplasmic tryptophanyl-tRNA synthetase, including portions of antibodies which can specifically recognize and bind to the cytoplasmic tryptophanyl-tRNA synthetase. These antibodies can be used in methods to detect and/or purify a protein of the present invention or portion thereof, for example by immunoaffinity chromatography, or to selectively inactivate an active site, or to study other aspects of enzyme structure, for example.

The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as an isolated and/or recombinant Candida cytoplasmic tryptophanyl-tRNA synthetase or portion thereof, or synthetic molecules, such as synthetic peptides. The immunogen, for example, can be a protein having at least one function that is characteristic of a Candida cytoplasmic tryptophanyl-tRNA synthetase, as described herein.

The term antibody is also intended to encompass single chain antibodies, chimeric, humanized or primatized (CDR-grafted) antibodies, and the like, as well as chimeric or CDR-grafted single chain antibodies, comprising portions from more than one species. For example, the chimeric antibodies can comprise portions of proteins derived from two different species, joined together chemically by conventional techniques or prepared as a contiguous protein using genetic engineering techniques (e.g., DNA encoding the protein portions of the chimeric antibody can be expressed to produce a contiguous protein chain). See, e.g., Cabilly, et al., U.S. Pat. No. 4,816,567; Cabilly, et al., European Patent No. 0,125,023 B1; Boss, et al., U.S. Pat. No. 4,816,397; Boss, et al., European Patent No. 0,120,694 B1; Neuberger, M. S., et al., WO 86/01533; Neuberger, M. S., et al., European Patent No. 0,194,276 B1; Winter, U.S. Pat. No. 5,225,539; Winter, European Patent No. 0,239,400 B1; Queen et al., U.S. Pat. No. 5,585,089; and Queen et al., European Patent No. EP 0 451 216 B1. See also, Newman, R., et al., *BioTechnology* 10: 1455–1460 (1992), regarding primatized antibody, and Ladner, et al., U.S. Pat. No. 4,946,778 and Bird, R. E., et al., *Science* 242: 423–426 (1988)) regarding single chain antibodies.

Whole antibodies and biologically functional fragments thereof are also encompassed by the term antibody. Biologically functional antibody fragments which can be used include those fragments sufficient for binding of the antibody fragment to a Candida cytoplasmic TrpRS to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen, and polyclonal and monoclonal antibody production can be performed using any suitable technique. A variety of methods have been described (see e.g., Kohler, et al., *Nature* 256: 495–497 (1975) and *Eur. J. Immunol.* 6:511–519 (1976); Milstein, et al., *Nature* 266: 550–552 (1977); Koprowski, et al., U.S. Pat. No. 4,172,124; Harlow, E. and Lane, D.; 1988, *Antibodies: A Laboratory Manual,* (Cold Spring Harbor Laboratory: Cold Spring Harbor, N.Y.); *Current Protocols In Molecular Biology,* Vol. 2 (Supplement 27, Summer '94), Ausubel, F. M., et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those obtained from the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can used, including, for example, methods which select recombinant antibody from a library (e.g., Hoogenboom et al. WO 93/06213; Hoogenboom et al. U.S. Pat. No. 5,565,332; WO 94/13804, published Jun. 23, 1994; and Dower, W. J., et al., U.S. Pat. No. 5,427,908), or which rely upon immunization of transgenic animals (e.g., mice) capable of producing a full repertoire of human antibodies (see e.g., Jakobovits et al., *Proc. Natl. Acad. Sci. USA*, 90:2551–2555 (1993); Jakobovits et al., *Nature*, 362:255–258 (1993); Lonberg et al., U.S. Pat. No. 5,569,825; Lonberg et al., U.S. Pat. No. 5,545,806; Surani et al., U.S. Pat. No. 5,545,807; and Kucherlapati, R. et al., European Patent No. EP 0 463 151 B1).

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more Candida cytoplasmic tryptophanyl-tRNA synthetases.

Enzyme Assay

Upon isolation from a species of the genus Candida, a cytoplasmic TrpRS gene can be incorporated into an expression system for production of the cytoplasmic TrpRS enzyme or a fusion protein, followed by isolation and testing of the enzyme in vitro. The isolated or purified Candida cytoplasmic TrpRSs can also be used in further structural studies that allow for the design of antibiotics which specifically target one or more aaRSs of Candida, while not affecting or minimally affecting host or mammalian (e.g., human) aaRSs. Because the amino acid sequences of the tRNA synthetases have diverged over evolution, significant differences exist between the structure of the enzymes from mammals (e.g., human, bovine) and mammalian pathogens, and the design or selection of inhibitors can exploit the structural differences between the pathogen aaRS and the host (e.g., a mammalian host, such a human) aaRS to yield specific inhibitors of the pathogen aaRS, which may further have antimicrobial activity.

Furthermore, isolated and/or recombinant, active Candida cytoplasmic TrpRSs can be used in an in vitro method of screening for inhibitors of cytoplasmic tryptophanyl-tRNA synthetase activity in which the inhibitory effect of a compound is assessed by monitoring cytoplasmic TrpRS activity according to standard techniques or other suitable methods. A composition comprising a (i.e., one or more) test compound (e.g., a mixture of compounds) can be used in the assay. For example, inhibitors of the activity of isolated, recombinant Candida cytoplasmic TrpRS can be identified by the method. Thus, the invention relates to a method of identifying an inhibitor of a Candida cytoplasmic TrpRS comprising contacting an isolated and/or recombinant protein or polypeptide of the present invention (e.g., a protein comprising a Candida cytoplasmic TrpRS or functional portion thereof), with a composition comprising one or more candidate inhibitors under conditions suitable for aminoacyl-tRNA synthetase activity, and monitoring activity. A decrease in activity relative to a suitable control (e.g., activity in the absence of the composition comprising inhibitor) is indicative that the composition contains one or more inhibitors of said Candida cytoplasmic TrpRS.

In one embodiment, the isolated cytoplasmic TrpRS enzyme is maintained under conditions suitable for tryptophanyl-adenylate formation, the enzyme is contacted with a compound to be tested, and formation of the tryptophanyl-adenylate or $PP_i$ is monitored. A reduction in the activity measured in the presence of compound, as compared with the activity in the absence of compound, is indicative of inhibition of cytoplasmic tryptophanyl-tRNA synthetase activity by the compound.

For example, the extent of tryptophanyl-adenylate formation catalyzed by purified cytoplasmic TrpRS can be measured using an ATP-pyrophosphate exchange assay in the presence and in the absence of a candidate inhibitor (Calendar, R. and Berg, P., *Biochemistry* 5:1690–1695 (1966)). In this reaction, the enzymatic synthesis of ATP from AMP and pyrophosphate in the absence of tRNA is monitored. A candidate inhibitor can be added to a suitable reaction mixture (e.g., 100 mM Tris-HCl, pH 7.5/5 mM $MgCl_2$/10 mM 2-mercaptoethanol/10 mM KF/2 mM ATP/2 mM [$^{32}$P]pyrophosphate/1 mM tryptophan), and the mixture is incubated at 25° C. Cytoplasmic TrpRS (to a final concentration of ~10 nM) is added to initiate the reaction. Aliquots of the reaction are removed at various times and quenched in 7% (vol/vol) cold perchloric acid, followed by the addition of 3% (wt/vol) charcoal suspended in 0.5% HCl. The ATP adsorbed to charcoal is filtered onto glass fiber pads (Schleicher & Schuell), and formation of [$^{32}$P] ATP is quantified by liquid scintillation counting in Hydrofluor (National Diagnostics, Manville, N.J.). The enzyme activity measured in the presence of the compound can be compared with the activity in the absence of the compound to assess the level of inhibition. Alternatively, a candidate inhibitor can be preincubated with enzyme under suitable conditions. Preincubation in the absence of substrate provides a more sensitive assay for the detection of inhibition (e.g., detects slow binding inhibitors). For example, the compound can be added to a mixture containing ~10 nM cytoplasmic tryptophanyl-tRNA synthetase in 100 mM Tris-HCl, pH 7.5/5 mM $MgCl_2$/10 mM 2-mercaptoethanol/10 mM KF, and preincubated at 25° C for 20 minutes. To initiate the reaction, ATP, [$^{32}$P]pyrophosphate and tryptophan are added to final concentrations of 2 mM, 2 mM and 1 mM, respectively. The reaction can be monitored as described above, and the activity measured in the presence of compound is compared with the activity in the absence of compound to assess inhibition.

In a further embodiment, formation of $PP_i$ can be monitored in a suitable assay. For example, TrpRS-dependent production of $PP_i$, which can occur in the presence of tryptophan, ATP and isoaccepting tRNA, can be monitored in a suitable assay. For example, TrpRS-dependent production of $PP_i$, in the presence of tryptophan, ATP and isoaccepting tRNA, can be monitored in the presence of inorganic pyrophosphatase, to generate two moles of phosphate ($P_i$) per mole of tryptophanyl-AMP formed. Phosphate production can be monitored in a coupled assay, for example by coupling to phosphorolysis of the chromogenic nucleoside 2-amino 6-mercapto 7-methylpurine ribonucleoside (AMMPR) catalyzed by excess purine nucleoside phosphorylase to yield ribose 1-phosphate and 2-amino 6-mercapto 7-methylpurine (AMMP). The absorbance at 360 nm of AMMP can be followed continuously by spectrophotometer (Lloyd, A. J. et al., *Nucl. Acids. Res.* 23:2886–2892 (1995)). It will be appreciated that other coupled assays can be used to monitor aaRS-dependent production of $PP_i$ in which the step following the conversion of $PP_i$ to phosphate requires phosphate and produces a product which can be quantitated. Such assays are also suitable for assessing formation of $PP_i$ by tryptophanyl-tRNA synthetases, in the presence of cognate amino acid and a corresponding isoaccepting tRNA.

In another embodiment, formation of the aminoacylated tRNA is monitored in an aminoacylation assay. Inhibitors identified by enzymatic assay can be further assessed for antimicrobial activity using tester strains as described herein, or using other suitable assays. For example, the extent of aminoacylation of tRNA with tryptophan catalyzed by cytoplasmic TrpRS (e.g., a GST fusion) can be measured by monitoring the incorporation of [$^3$H]tryptophan into trichloroacetic acid-precipitable [$^3$H]tryptophanyl-tRNA in the presence of a candidate inhibitor, as compared with activity in the absence inhibitor. Appropriately diluted cytoplasmic TrpRS can be preincubated for 20 minutes at 25° C. in, for example, 50 mM HEPES, pH 7.5/0.1 mg/ml BSA (bovine serum albumin)/10 mM $MgCl_2$/10 mM 2-mercaptoethanol/20 mM KCl/1–20% DMSO (preferably about 1%) in the presence or absence of a compound to be tested. The preincubation mixture can be supplemented with ATP, [$^3$H]tryptophan and tRNA to final concentrations of, for example, 4 mM ATP/20 $\mu$M [$^3$H]tryptophan (0.6 $\mu$Ci), and 90 $\mu$M crude tRNA or 2 $\mu$M specific tRNA$^{Trp}$. The reaction is maintained at 25° C., and aliquots are removed at specific times, and applied to filter paper discs (3 MM, Whatman) that have been presoaked with 5% (wt/vol) trichloroacetic acid. Filters are washed for three 10-minute periods in 5% trichloroacetic acid, rinsed in 95% ethanol and 100% ether, and the incorporation of $^3$H-tryptophan into tRNA (formation of $^3$H-Trp-tRNA) can be measured in Betafluor by liquid scintillation counting. The amino acylation assay can also be performed without preincubation under suitable conditions (e.g., using ~0.4 nM cytoplasmic TrpRS in a reaction mixture containing 50 mM HEPES, pH 7.5/0.1 mg/ml BSA (bovine serum albumin)/10 mM $MgCl_2$/ 10 mM, 2-mercaptoethanol/20 mM KCl/1–20% DMSO/4 mM ATP/20 $\mu$M [$^3$H]tryptophan (0.6 $\mu$Ci), and 90 $\mu$M crude tRNA or 2 $\mu$M specific tRNA$^{Trp}$) in the presence or absence of test compound. An $IC_{50}$ value (the concentration of inhibitor causing 50% inhibition of enzyme activity) for a known amount of active cytoplasmic TrpRS can be determined.

Binding Assay

An isolated, recombinant aaRS or a portion thereof, and suitable fusion proteins can be used in a method to select and identify compounds which bind specifically to Candida cytoplasmic TrpRSs, such as *C. albicans* cytoplasmic tryptophanyl-tRNA synthetase, and which are potential inhibitors of cytoplasmic TrpRS activity. Compounds selected by the method can be further assessed for their inhibitory effect on cytoplasmic TrpRS activity and for antimicrobial activity.

In one embodiment, an isolated or purified Candida cytoplasmic TrpRS can be immobilized on a suitable affinity matrix by standard techniques, such as chemical cross-linking, or via an antibody raised against the isolated or purified cytoplasmic TrpRS, and bound to a solid support. The matrix can be packed in a column or other suitable container and is then contacted with one or more compounds (e.g., a mixture) to be tested under conditions suitable for binding of compound to the cytoplasmic TrpRS. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more substrates or substrate analogs which can disrupt binding of compound to the cytoplasmic TrpRS, such as tryptophan, ATP, tRNA$^{Trp}$, or other suitable molecules which competitively inhibit binding).

Fusion proteins comprising all of, or a portion of, the cytoplasmic TrpRS linked to a second moiety not occurring in the Candida cytoplasmic TrpRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of an cytoplasmic TrpRS gene or portion thereof into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the cytoplasmic TrpRS portion of the bound fusion protein. Next, the affinity matrix with bound fusion protein can be washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer can be formulated to permit binding of the fusion protein to the affinity matrix, without significantly disrupting binding of specifically bound compounds. In this aspect, compound elution buffer can be formulated to permit retention of the fusion protein by the affinity matrix, but can be formulated to interfere with binding of the compound(s) tested to the cytoplasmic TrpRS portion of the fusion protein. For example, a change in the ionic strength or pH of the elution buffer can lead to release of compounds, or the elution buffer can comprise a release component or components designed to disrupt binding of compounds to the cytoplasmic TrpRS portion of the fusion protein (e.g., one or more substrates or substrate analogs which can disrupt binding of compounds to the cytoplasmic TrpRS portion of the fusion protein, such as tryptophan, ATP, or tRNA$^{Trp}$, or other suitable molecules which competitively inhibit binding).

Immobilization can be performed prior to, simultaneous with, or after contacting the fusion protein with compound, as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the cytoplasmic TrpRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the cytoplasmic TrpRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J., et al., *Proc. Natl. Acad. Sci. USA* 90:10922–10926 (1993) and DeWitt, S. H., et al., *Proc. Natl. Acad. Sci. USA* 90:6909–6913 (1993), relating to tagged compounds; see also Rebek, et al., Process for Creating Molecular Diversity, U.S. Ser. No. 08/180,215, filed Jan. 12, 1994, relating to compounds without tags; see also, Rutter, W. J., et al., U.S. Pat. No. 5,010,175; Huebner, V. D., et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries (see Ellington, A. D., et al., *Nature* 346: 818–822 (1990); Bock, L. C., et al., *Nature* 355: 584–566 (1992); and Szostak, J. W., *Trends in Biochem. Sci.* 17:89–93 (March 1992)) can also be screened according to the present method to select RNA or DNA molecules which bind to a Candida cytoplasmic TrpRS. Such molecules can be further assessed for antimicrobial effect upon introduction into a cell (e.g., by expression in the case of an RNA molecule selected by the method).

Tester Strains

Nucleic acids of the present invention can also be used in constructing tester strains for in vivo assays of the effect on the activity of the Candida enzyme of a substance which is added to tester strain cells. A tester strain comprises a host cell having a defect in a gene encoding an endogenous aaRS, and a heterologous aaRS gene which complements the defect in the host cell gene. Thus, complementation of a particular defective host cell aaRS gene by a heterologous aaRS gene is a threshold requirement for a tester strain. Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

If the heterologous gene complements the inactivated host cell gene, such a cell can be used to determine whether a substance that is introduced into the cells for testing, can interact specifically with the heterologous tRNA synthetase (or a component in the pathway of the expression of the heterologous tRNA synthetase gene) to cause loss of function of the tested heterologous tRNA synthetase in those host cells. Thus, such cells are "tester strains". Successful cross-species complementation has been described, for example, for yeast seryl-tRNA synthetase and for yeast isoleucyl-tRNA synthetase in *E. coli* (Weygand-Durasevic, I., et al., *Eur. J. Biochem* 214:869–877 (1993); Racher, K. I., et al., *J. Biol. Chem.* 266:17158–17164 (1991)).

In tester cells to be used in an assay for chemical substances that can inhibit the function of a specific aaRS, the gene for the aminoacyl-tRNA synthetase can, for example, physically replace the host cell aaRS gene or can be present in addition to a host aaRS gene that does not produce a functional product, and the heterologous gene whose gene product is to be tested complements the host gene. A substance to be tested is administered to the tester cells, and the viability or growth of such cells can be compared with that of cells of a suitable control.

As a tester strain comprises a host cell comprising a heterologous aaRS gene (i.e., one from a heterologous species), a suitable host cell is heterologous with respect to the species from which the gene to be tested is isolated. For instance, suitable host cells to test *Candida albicans* genes can be host cells of a species other than *C. albicans*. Examples of species which are suitable for use as hosts for the construction of tester strains are *E. coli, B. subtilis,* and *S. cerevisiae*. These species are especially amenable to genetic manipulation because of their history of extensive study.

Suitable host cells having a genotype useful for the construction of a tester strain can be constructed or selected using known methods. For example, both in *E. Coli* and in *S. cerevisiae,* a first plasmid which contains a functional copy of a host chromosomal aaRS gene (which is to be inactivated later), and some selectable marker gene, can be constructed and introduced into cells. Then, an inactivating mutation can be caused in the chromosomal copy of the aaRS gene.

This can be accomplished, for instance, by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin, et al., U.S. Pat. No. 4,713,337; Schimmel, P., U.S. Pat. No. 4,963,487; Toth, M. J. and Schimmel, P., *J. Biol. Chem.* 261:6643–6646 (1986); Rothstein, R., *Methods in Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS.

A test plasmid which is compatible with the maintenance plasmid, and which contains the aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluororotic acid to select against *S. cerevisiae* cells which have a first plasmid containing the URA3 gene), cells which survive by virtue of having a complementing aaRS gene on the second plasmid can be selected (Sikorsky, R. S. and Boeke, J. D., *Methods in Enzymology* 194:302–318 (1991)).

Causing or selecting for a double crossover event which creates a deletion and insertion can be used in itself as a one-step method of constructing a tester strain in which a native aaRS gene is replaced by the corresponding foreign gene whose gene product is to be tested. Endogenous recombination mechanisms have been used to advantage previously in *E. coli, B. subtilis,* and *S. cerevisiae,* among other organisms. This method depends on the ability of the heterologous gene to be tested to complement the native corresponding aaRS gene. This can be done by introducing into the cells double-stranded DNA having regions of homology to the DNA flanking the target native aaRS gene, and having between these regions a gene encoding a selectable marker as well as the heterologous aaRS gene intended to replace the native aaRS gene. The survival of cells expressing the selectable marker is indicative of expression of the introduced heterologous aaRS gene and complementation of the defect in the endogenous synthetase.

For example, a tester strain useful for testing the effect of a compound on the function of cytoplasmic TrpRS expressed by an inserted *C. albicans* gene, can be constructed in a one-step method in a suitable host cell. Optional positive and negative controls for this cross-species transformation can be used to show that the resulting strain depends on the cytoplasmic TrpRS gene from *C. albicans* for growth and that this recombination event is not lethal. For example, *S. cerevisiae* cells can be transformed with a suitable construct, such as a linearized plasmid containing an insert. Generally, the construct includes a selectable marker gene for antibiotic resistance, or other suitable selectable marker. In one embodiment, a linearized plasmid which contains the *C. albicans* cytoplasmic TrpRS gene and an antibiotic resistance gene, situated between sequences homologous to the flanking sequences of the endogenous cytoplasmic TrpRS gene of the host cells, is used to transform the host cell. For a positive control, the linearized plasmid can be constructed in a similar fashion, except that the native *S. cerevisiae* cytoplasmic TrpRS gene replaces the *C. albicans* gene, such that a normal *S. cerevisiae* cytoplasmic TrpRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous cytoplasmic TrpRS gene. Successful construction of a tester strain can also be confirmed by Southern analysis.

In cases of gene duplication (LysU and LysS in *E. coli* a (Kawakami, K., et al., *Mol. Gen. Genet.* 219:333–340 (1989); Leveque, F., et al., *Nucleic Acids Res.* 18:305–312 (1990); Clark, R. L. and Neidhardt, F. C., *J. Bacteriol.* 172:3237–3243 (1990)), or the presence of a cryptic gene (tyrZ in *B. subtilis*, Glaser, P., et al., *DNA Sequ. and Mapping* 1:251–61 (1990); Henkin, T. M., et al., *J. Bacteriol.* 174:1299–1306 (1992), a suitable tester strain can be constructed by simultaneous inactivation of both of the host genes, or by sequential inactivation. For instance, inactivation of one host gene by a suitable method, such as by insertion of a selectable marker, can be followed by a one-step gene replacement of the remaining host gene with a heterologous Candida aaRS gene and a second selectable marker.

The yeast *S. cerevisiae* offers additional possibilities for genetic manipulations to create tester strains, relative to bacteria. Yeast integrating plasmids, which lack a yeast origin of replication, can be used for making alterations in the host chromosome (Sikorski, R. S. and Hieter, P., *Genetics* 122:19–27 (1989); Gietz, R. D. and Sugino, A., *Gene* 74:527–534 (1988)). In another embodiment, one-step gene disruptions can be performed in diploid cells using a DNA fragment comprising a copy of an aaRS gene (optionally containing a deletion in the aaRS gene) having an insertion of a selectable marker in the aaRS gene. A suitable fragment can be introduced into a diploid cell to disrupt a chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the heterologous aaRS gene. These cells can be sporulated and the haploid spores analyzed for rescue of the defective chromosomal aaRS by the heterologous aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid host strain can then be transformed with a test plasmid which expresses a heterologous aaRS gene, and the maintenance plasmid can be selected against by growing this strain under appropriate conditions.

Construction of a tester strain may start with the isolation of a mutant host strain which produces, for example, an inactive tRNA synthetase specific for a particular amino acid, a tRNA synthetase which is conditionally inactivitable, or which carries a chromosomal deletion of a tRNA synthetase. A number of *E. coli* and *S. cerevisiae* strains have been described that can be used for constructing tester strains. Some of these strains are described below for illustrative purposes. The procedures used to isolate and/or construct these *E. coli* and *S. cerevisiae* strains, or similar procedures, can be used or adapted to make additional mutant strains in *E. coli, S. cerevisiae* or other host organisms.

*E. coli* strains having a defect, such as a null mutation, in an aminoacyl-tRNA synthetase gene can be constructed using a cloned *E. coli* aaRS gene. Each aminoacyl-tRNA synthetase from *E. coli* has been cloned (see Meinnel, T., et al., 1995, "Aminoacyl-tRNA Synthetases: Occurrence, Structure and Function," In: *tRNA: Structure, Biosynthesis and Function*, Söll, D. and RajBhandary, U., Eds., (American Society for Microbiology: Washington, D.C.), Chapter 14, pp. 251–292, the teachings of which are incorporated herein by reference). The cloned genes can be incorporated into a suitable construct and be used as maintenance plasmids in a suitable host cell.

A number of *E. coli* strains have been characterized in which an aaRS gene has been inactivated by some method, in whole or in part, yielding an observable phenotypic defect which can be detectably complemented. For example, null strains in which the gene encoding IleRS has been inactivated (IQ843, IQ844, see Shiba, K. and Schimmel, P., inactivated (IQ843, IQ844, see Shiba, K. and Schimmel, P., *J. Biol. Chem.* 267:22703–22706 (1992)), and a mutant strain (MI1, see Starzyk, et al., *Science* 237:1614–1618 (1987) and Iaccarino and Berg, *J. Bacteriol.* 105:527–537 (1970)) having an isoleucine auxotrophy due to an elevated $K_m$ for isoleucine of the enzyme encoded by the chromosomal ileS allele, have been described. Both temperature sensitive and auxotrophs for TrpRS have been described in *E. coli*, Bohman, K. and Isaksson L. A., *Mol. Gen. Genet.* 161:285 (1978); Russel R. R. B. and Pittard, A. J., *J. Bacteriol.* 108:790–798 (1971); Doolittle W. F. and C. Yanofsky, *J. Bacteriol.* 95:1283 (1968); Kano, Y. et al., *Mol. Gen. Genet.* 102:99–124 (1968)).

E. coli strain IQ843/pRMS711 and its derivative IQ844/pRMS711 contain a chromosomal deletion of the ileS gene (ΔileS203::kan), and are propagated by expression of wild type IleRS at 30° C. from a temperature-sensitive maintenance plasmid designated pRMS711, which encodes the wild type ileS gene and a gene which confers chloramphenicol resistance. pRMS711 cannot replicate at 42° C.; thus, at the non-permissive temperature, the maintenance plasmid is lost. Following the introduction of a test construct into these strains, the growth of chloramphenicol sensitive colonies at a non-permissive temperature (e.g., 42° C.) is indicative of complementation of the chromosomal ileS deletion by the introduced construct (Shiba, K. and Schimmel, P., *Proc. Natl. Acad. Sci. USA* 89:1880–1884 (1992); Shiba, K. and Schimmel, P., *Proc. Natl. Acad. Sci. USA* 89:9964–9968 (1992); Shiba, K. and Schimmel, P., *J. Biol. Chem.* 267:22703–22706 (1992)).

Temperature sensitive alleles are examples of genes encoding conditionally inactivatable tRNA synthetases. For example, temperature-sensitive alleles of the genes encoding cytoplasmic IleRS (ils1-1) and MetRS (mes1-1) have been described in *S. cerevisiae* (Hartwell, L. H., and McLaughlin, and Hartwell, L. H., *Genetics* 61:557–566 (1969)), and are available from the Yeast Genetic Stock Center (University of California-Berkeley; catalog nos. 341 and 19:3:4, respectively).

The *S. cerevisiae* genome has been fully sequenced and all of the aminoacyl-tRNA synthetases have been identified. For construction of a tester strain in *S. cerevisiae*, a plasmid which contains the wild type cytoplasmic tryptophanyl-tRNA synthetase gene of *S. cerevisiae* can be used to construct a mutant strain, and for the construction of maintenance plasmids to create cytoplasmic tester strains for a TrpRS.

Strains having a defect in mitochondrial aminoacyl-tRNA synthetase can be constructed using a cloned mitochondrial aaRS gene, and used to make tester strains (see Meinnel, T. et al., 1995, "Aminoacyl-tRNA synthetases: Occurrence, Structure and Function", In: *tRNA: Structure, Biosynthesis and Function*, Söll, D. and RajBhandary, U, Eds., American Society for Microbiology: Washington, D.C., Chapter 14, pp. 251–292; also see ATCC Catalog of Recombinant DNA Materials, American Type Culture Collection, Rockville, Md., regarding mitochondrial aaRS genes). For example, an *S. cerevisiae* strain has been constructed which carries a disruption of MSY1, the gene encoding mitochondrial tyrosyl-tRNA synthetase. Plasmids carrying MSY1 which rescue this defect, also have been constructed (Hill, J. and Tzagoloff, A., Columbia University; see Edwards, H. and Schimmel, P., *Cell* 51:643–649 (1987)).

In *S. cerevisiae*, to construct a maintenance plasmid or a test plasmid carrying a heterologous gene, a suitable vector, such as a yeast centromere plasmid (CEN; single-copy) or 2μ vector (high copy) can be used. A heterologous gene to be tested can also be incorporated into the chromosome, using an integrating plasmid, for example. Examples of convenient yeast vectors for cloning include vectors such as those in the pRS series (integrating, CEN, or 2μ plasmids differing in the selectable marker (HIS3, TRP1, LEU2, URA3); see Christianson, T. W., et al., *Gene* 110:119–122 (1992) regarding 2μ vectors; see Sikorski, R. S. and Hieter, P., *Genetics* 122:19–27 (1989) regarding integrating and CEN plasmids which are available from Stratagene, La Jolla)) and shuttle vectors (integrating, CEN or 2μ vectors) which contain the multiple cloning site of pUC19 (Gietz, R. D. and Sugino, A., *Gene* 74:527–534 (1988)). Examples of expression vectors include pEG (Mitchell, D. A., et al., *Yeast* 9:715–723 (1993)) and pDAD1 and pDAD2, which contain a GAL1 promoter (Davis, L. I. and Fink, G. R., *Cell* 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehyrogenase; Bennetzen, J. L. and Hall, B. D., *J. Biol. Chem.* 257:3026–3031 (1982)) can be used to express an inserted gene on glucose-containing media.

For illustration, a yeast tester strain can be constructed as follows. A *Saccharomyces cerevisiae* strain with convenient markers, such as FY83 (MATa/MATα lys2-128δ/lys2-128δ leu2Δ1/leu2Δ1 ura3-52/ura3-52 trp1Δ63/trp1Δ63) can be used as a host cell.

A nucleic acid encoding a yeast cytoplasmic aaRS can be used to create a null allele of the yeast cytoplasmic aaRS gene. For example, a deletion/insertion allele can be constructed by excising the aaRS open reading frame, including the promoter region and 3' flanking region or portions thereof from a cloned gene, and replacing the excised sequence with a selectable marker (e.g., TRP1). This aaRS::TRP1 fragment can be used to transform the diploid strain FY83, and Trp$^+$ transformants can be selected (Rothstein, J., *Methods in Enzymol.* 101:202–211 (1983)). Standard genetic procedures can be employed to identify the appropriate integrant created by this one-step gene disruption (a diploid having the genotype MATa/MATα lys2-128δ/lys2-128δ leu2Δ1/leu2Δ1 ura3-52/ura3-52 trp1Δ63/trp1Δ63 aaRS::TRP1/aaRS); Rose, M. D., et al., *Methods in Yeast Genetics*, 1990, Cold Spring Harbor Press, Cold Spring Harbor, N.Y.).

To construct a maintenance plasmid, a fragment containing the aaRS coding region, its promoter and some of the 3' untranslated region (e.g., a region approximately equivalent to that deleted in the construction of the null allele above) can be excised and introduced into a vector such as YCplac33, a CEN plasmid containing a URA3 selectable marker (Gietz, R. D. and Sugino, A., *Gene* 74:527–534 (1988)). The resulting plasmid can be used to transform the aaRS::TRP1/aaRS diploid described above, and Ura$^+$ transformants which contain the maintenance plasmid can be selected. The resulting diploid can be sporulated and a haploid Trp$^+$Ura$^+$ spore (an aaRS null strain), corresponding to a aaRS::TRP1 strain dependent upon the URA3- aaRS maintenance plasmid can be isolated.

To construct a test plasmid (a plasmid bearing a heterologous tRNA synthetase gene to be tested for its ability to complement the defect in the endogenous yeast gene), a heterologous aaRS gene to be tested can be inserted into a suitable vector for expression. For instance, a multicopy vector. A fragment containing the *C. albicans* aaRS gene can be inserted into the vectors, using one or more suitable restriction sites in the multiple cloning site, for example. Alternatively, to test whether a relatively reduced level of expression of the heterologous tRNA synthetase gene permits complementation, a fragment containing the *C. albicans* aaRS gene can be inserted into a CEN plasmid for expression. Preferably, the heterologous gene is inserted into the vector so that its ATG start codon is the first ATG within 50 to 100 bp of the transcription start site of the ADH promoter of the vector.

Because these plasmids bear the LEU2 selectable marker, they can be used to transform a null strain, such as the Trp$^+$Ura$^+$Leu- strain described, and Leu$^+$ transformants containing the test plasmid can be selected. Leu$^+$Ura$^+$Trp$^+$ transformants (containing a aaRS::TRP1 allele, a URA3 maintenance plasmid, and the LEU2 test plasmid) can be tested for growth on media containing 5-fluoroorotic acid (5-FOA). 5-FOA is toxic to URA3 cells, and causes loss of the URA3 maintenance plasmid (Boeke, J., et al., *Mol. Gen. Genet.* 197:345–346 (1984)). Accordingly, growth of cells on media containing 5-FOA is indicative of complementation of the lethal deletion in the aaRS gene on the chromosome (aaRS::TRP1) by the heterologous aaRS gene on the test plasmid. Cells that are unable to grow on 5-FOA are dependent upon the maintenance plasmid for viability, and therefore, are indicative of insufficient activity to complement the lethal deletion in the aaRS gene. Where complementation is observed, the strain can be used to test for inhibitors of the product of the heterologous gene encoded by the test plasmid.

In another embodiment, a mitochondrial tryptophanyl-tRNA synthetase gene disruption with a cosegregating selectable marker can be constructed in a diploid rho$^+$ strain (see e.g., Edwards, H. and Schimmel, P., *Cell* 51:643–649 (1987)). A plasmid encoding a Candida tryptophanyl-tRNA synthetase gene is introduced on a plasmid having a second selectable marker. Sporulation of a resulting diploid yields two progeny spores carrying the yeast mitochondrial tryptophanyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the Candida gene on the introduced plasmid is indicated by growth on non-fermentable carbon sources of spores carrying the disrupted tryptophanyl-tRNA synthetase gene.

In the case of a mitochondrial tester strain, the Candida aminoacyl-tRNA synthetase can be imported into mitochondria to achieve complementation of the mitochondrial defect. When it is necessary to achieve import or desirable to improve the efficiency of import of the aminoacyl-tRNA synthetase in the host cell, a gene fusion can be constructed using a sequence encoding a mitochondrial targeting sequence which functions in the host cell. For example, a mitochondrial targeting sequence can be introduced at the amino-terminal end of the Candida aminoacyl-tRNA synthetase. In one embodiment in yeast, the Candida aaRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus, et al., *J. Biol. Chem.* 263:13097 (1988)). Expression of the construct yields a fusion protein with an N-terminally located cytochrome oxidase IV targeting signal joined to the Candida aaRS protein.

If the construction methods described here are not successful initially, one or more natural or synthetic Candida or other (e.g., procaryotic, such as a bacterial, or eukaryotic, such as a mammalian or fungal) tRNA gene(s) can be introduced into the host cell to provide one or more cognate tRNAs for the Candida aaRS. The tRNA genes of a number of species have been cloned and sequenced (Steinberg, S., et al., "Compilation of tRNA sequences and sequences of tRNA genes", *Nucleic Acids Res.* 21:3011–3015 (1993)). A method for constructing a strain of *Streptomyces lividans* in which an essential tRNA gene has been inactivated in the chromosome, and the gene is instead maintained on a plasmid, has been described (Cohen, S.N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous aminoacyl-tRNA synthetase gene present in the tester strain (i.e., the "test gene"), can serve as control strains. These control strains comprise a "control gene" which is an aminoacyl-tRNA synthetase gene other than the heterologous Candida aaRS gene present in the tester strain (i.e., an aaRS gene from a different species, such as a procaryotic or eukaryotic species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain, and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having a *C. albicans* aaRS gene, an *E. coli* strain having a wild-type *E. coli* control gene can be used as a control strain.

In another embodiment, the control strain can be a strain distinct from the tester strain, which is constructed in a manner which generally parallels that of the tester strain comprising the test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene," which, as indicated above, is an aaRS gene other than the test gene (i.e., an aaRS gene from a different species, such as a heterologous procaryotic or eukaryotic species). Furthermore, the control gene encodes an aaRS specific for the same amino acid as the test gene. Preferably, the control gene is selected from a species which is a host for the pathogen from which the test gene is derived, permitting the identification of specific inhibitors which selectively inhibit the pathogen aaRS (e.g., human control gene for an *C. albicans* test gene). Alternatively, because the eukaryotic aminoacyl-tRNA synthetases are generally more closely related to each other than to procaryotic aminoacyl-tRNA synthetases, a control gene from another eukaryote (e.g., a different mammalian species) can be used in lieu of one selected from the host species (e.g., a rat or mouse control gene for an *C. albicans* test gene).

For example, a strain isogenic with a tester strain, except for the substitution of a human control gene, can serve as a control strain. Such a control strain can be constructed using the same methods and the same host cell used to construct the tester strain, with the exception that a human control gene is introduced into the host cell in lieu of the heterologous Candida aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising a *C. albicans* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous Candida aaRS encoded by the test gene (or a step in the expression of the Candida gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target aminoacyl-tRNA synthetase, such as a *C. albicans* cytoplasmic TrpRS, could reduce the effectiveness of an inhibitor of aaRS activity. To test for mutations that confer resistance to an inhibitor (e.g., an inhibitor of aaRS activity, including such an inhibitor having antimicrobial activity) a variety of approaches can be used. Mutant Candida aaRS genes can be obtained, for example, by isolation of a mutant gene, or by preparing an individual mutant gene or an expression library of mutant Candida aaRS genes, such as a library of mutants of a *C. albicans* cytoplasmic TrpRS gene. The mutant gene or gene library can be introduced into suitable host cells for screening for resistance to a compound.

An isolated tRNA synthetase gene, such as a *C. albicans* aaRS gene, can be mutagenized by any suitable method including, but not limited to, cassette mutagenesis, PCR mutagenesis (e.g., the fidelity of PCR replication can be reduced to induce mutation by varying $Mg^{2+}$ concentration, increasing the number of amplification cycles, altering temperatures for annealing and elongation, to yield random mutants), or chemical mutagenesis (e.g., nitrosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., *E. coli*, yeast, *Bacillus subtilis*) aminoacyl-tRNA synthetase specific for the same amino acid, the mutant genes can be introduced into the wild-type host and the resulting cells can be exposed to drug to assess resistance.

In another embodiment, the procedures described above relating to tester strains are used in the method to identify mutants resistant to inhibitor. Introduction of the heterologous mutant aaRS gene(s) (i.e., mutant test gene(s)) into a host cell is carried out as described above for the production of tester strains. Using MetRS as an example, the library can be introduced into a host cell having a defect in the endogenous gene encoding MetRS. The metG null strain of *E. coli* designated MN9261/pRMS615 is an example of the type of strain that can be constructed and used as a host for the introduction of mutant Candida aaRS gene(s) (in that case, MetRS genes; see Kim, et al., *Proc. Natl. Acad. Sci. USA* 90:10046–10050 (1993), describing a strain which carries a null allele of metG, and a temperature sensitive maintenance plasmid, carring a wild type metG allele (encoding *E. coli* MetRS) and having a temperature sensitive replicon which causes loss of the maintenance plasmid at the nonpermissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., an active recombinant *C. albicans* cytoplasmic TrpRS) are identified by complementation of the host cell defect. Where complementation occurs, each resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of the metG null strain, complementation by the Candida gene is indicated by growth at the non-permissive temperature at which the maintenance plasmid is lost. Cells which survive loss of the maintenance plasmid due to the presence of the complementing mutant gene are then challenged with inhibitor to assess resistance. Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant Candida aaRS gene which confers resistance to an inhibitor upon a Candida cell, can be isolated from the Candida organism using nucleic acids of the present invention as probes. The cloned gene can then be introduced into a host cell as described for the production of tester strains. Tester cells comprising the mutant test gene which confers resistance, and which complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

Proteins of the present invention or stable subdomains of the protein can be used in a method to separate tryptophan from a mixture of tryptophan and other compounds such as other amino acids, or to specifically isolate L-tryptophan from D-tryptophan. For example, the cytoplasmic tryptophanyl-tRNA synthetase can be chemically attached to a solid support material packed in a column or other suitable container. Alternatively, a fusion protein, such as a GST-tRNA synthetase fusion or a His tag-tRNA synthetase fusion (having a histidine hexamer tail), can permit attachment to a suitable solid support which binds the GST portion or His tag portion of the fusion protein, respectively. For example, a mixture of tryptophan and other compounds can be loaded onto a column under conditions in which tryptophan binds to cytoplasmic tryptophanyl-tRNA synthetase, while other compounds present in the mixture flow through the column. In a later step, tryptophan can be released from cytoplasmic tryptophanyl-tRNA synthetase by changing the conditions in the column, such as washing with a solution of high ionic strength to elute L-tryptophan, for example.

In a similar manner, the cytoplasmic tryptophanyl-tRNA synthetase can be used in a method to isolate tRNA that is specifically recognized by the tRNA synthetase.

Candida cytoplasmic tryptophanyl-tRNA synthetases or functional portions thereof can be used in the quantitative determination of tryptophan by its conversion to the corresponding aminoacyl-hydroxamate (tryptophanyl-hydroxamate). An example of an appropriate assay is illustrated by the following series of reactions.

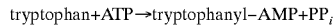
tryptophan+ATP→tryptophanyl-AMP+PP$_i$ (in the presence of excess pyrophosphatase and ATP at pH 7.5, where pyrophosphatase catalyzes the conversion of the product inorganic pyrophospate (PP$_i$) to inorganic orthophospate (P$_i$); ATP is adenosine triphospate; AMP is adenosine monophosphate)

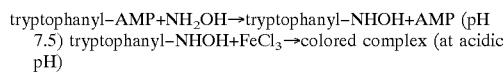
tryptophanyl-AMP+NH$_2$OH→tryptophanyl-NHOH+AMP (pH 7.5) tryptophanyl-NHOH+FeCl$_3$→colored complex (at acidic pH)

The resulting colored complex can be quantitated by spectrophotometric measurements of absorbance at 540 nm, and compared with a standard curve made using known concentrations of tryptophan. This assay is based on the reactions described by Stulberg and Novelli, *Methods in Enzymology* 5:703–707 (1962).

The Candida cytoplasmic tryptophanyl-tRNA synthetases can also be used for the quantitative determination of ATP. In the presence of excess amino acid such as tryptophan, and in the presence of pyrophosphatase to convert the product PP$_i$ to P$_i$, the ATP is quantitatively converted to AMP and inorganic pyrophosphate by the tryptophanyl-tRNA synthetase. For example,

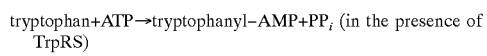
tryptophan+ATP→tryptophanyl-AMP+PP$_i$ (in the presence of TrpRS)

PP$_i$+H$_2$O→2P$_i$ (in the presence of pyrophosphatase)

P$_i$ can be quantitated by reaction with molybdate, measuring the absorbance at 580 nm and comparing to a standard curve made using known quantities of orthophosphate. Thus, the proteins can be used in coupled assays, in which the progress of an ATP-producing reaction is monitored.

Exemplification

The present invention will now be illustrated by the following Examples, which are not intended to be limiting in any way.

Materials and Methods

All restriction enzymes were purchased from New England Biolabs (Beverly, Mass.) unless otherwise stated. Ultrapure deoxynucleotide triphosphates (dNTPs) were purchased from Pharmacia. Overnight refers to more than 8 hours (up to 16 hours). Radioactive compounds were purchased from Dupont NEN. All bacterial transformations were done with the CaCl$_2$ procedure, unless otherwise stated. Sequencing was done using the Sequenase kit from USB. Procedures for standard techniques (e.g. bacterial transformation) and reagent preparation (e.g. TAE buffer) were done as described in Sambrook, J., et al., *Molecular Cloning: A Laboratory Manual,* 2nd Ed., Cold Spring Harbor Laboratory, Cold Spring Harbor, N.Y. (1989). Media for yeast cultures and experimental techniques used for yeast manipulations were as described in *Methods in Yeast Genetics: A Laboratory Manual* Rose, M. D., F. Winston and P. Hieter, eds., Cold Spring Harbor Laboratory Press, Cold Spring Harbor, N.Y. (1990).

Abbreviations

PCR=polymerase chain reaction; ORF=open reading frame; IPTG=isopropyl-β-D-thio-galactopyranoside; LB=Luria Broth EDTA=ethylenediaminetetraacetic acid; DTT=dithiothreitol; PBS=phosphate buffered saline; BSA= bovine serum albumin; TCA=tricholoracetic acid; SDS= sodium dodecyl sulfate

EXAMPLE 1

PCR Amplification of DNA Fragments of Cytoplasmic Tryptophanyl-tRNA Synthetase Genes From *C. albicans* Genomic DNA Polymerase chain reaction (PCR) was used to obtain DNA fragments of tryptophanyl-tRNA synthetase (TrpRS) genes using genomic DNA from *C. albicans* strain SC5314 as template (Gillum, A. et al., *Mol. Gen. Genet.* 198:179–182 (1984); a gift of Brendan Cormack, Stanford University). The PCR primers were designed to contain coding sequences for highly conserved regions in TrpRSs. Conserved regions were found by aligning the amino acid sequences of TrpRSs from several different eukaryotic organisms, using the Multiple Sequence Alignment Program from the Lasergene System (DNAStar, Inc., Madison, Wis.) using default parameters with the Clustal program and the PAM250 residue weight table (for the Clustal program, see Higgins, D. G. and P. M. Sharp, *Gene,* 73:237–244 (1988)). The following sequences retrieved from GenBank were used in the multiple alignments of TrpRS amino acid sequences: *H. sapiens* (Frolova, L. Yu., et al., *Gene* 109:291–296 (1991)), *B. taurus* (Garret, M. et al., *Biochemistry* 30:7809–7817 (1991)), *O. cuniculus* (Lee, C. C. et al., *Proc. Natl. Acad. Sci. U.S.A.* 87:3508–3512 (1990)), *M. musculus* (Pajot, B., et al., *J. Mol. Biol.* 242:599–603 (1994)), *S. cerevisiae* (Vandenbol, M. et al., *Yeast* 11: 1069–1075 (1995)) and *S. pombe* (Barrell, B. G. et al. unpublished), (GenBank Accession No.: Z50142).

Several conserved regions were chosen for the design of degenerate oligonucleotides which were used to generate PCR fragments of the *Candida albicans* cytoplasmic TrpRS gene. Table 1 shows the sequence of the degenerate oligonucleotide primers used for PCR amplification of the *C. albicans* cytoplasmic tryptophanyl-tRNA synthetases.

TABLE 1

Sequences of Degenerate PCR Primers Used for Amplification of *C. albicans* Tryptophanyl-tRNA Synthetases

| PRIMER NAME | SEQ ID NO. | PRIMER SEQUENCE (5'->3') |
|---|---|---|
| CaW-1# | 1 | GAR CAR RTI GTI ACI CCI TGG |
| CaW-3# | 2 | ACR TCI ACR TCI GGR TTI CCI CC |

TABLE 1-continued

Sequences of Degenerate PCR Primers Used for Amplification of *C. albicans* Tryptophanyl-tRNA Synthetases

| PRIMER NAME | SEQ ID NO. | PRIMER SEQUENCE (5'->3') |
|---|---|---|
| CaW-4# | 3 | GAR AAY GCI AAR GAY AT |
| CaW-5# | 4 | GGR TCY TGR TCD ATI GCR CAI GG |
| PCT-2 | 5 | TTY AAY CAR GTI AAR GGI ATI TTY GG |

R = A or G, Y = C or T, D = A, G, or T; I = inosine.

Unless otherwise stated, each PCR amplification described in the exemplification using degenerate oligonucleotides as primers was done in a 50 μl volume with 200 ng of *Candida albicans* genomic DNA from strain SC5314 (provided by Brendan Cormack, Stanford University), 40 pmoles of each primer, 10 mM Tris-HCl pH 8.3, 50 mM KCl, 1.5 mM MgCl$_2$, 100 μM of each dNTP, and 1.25 units of Taq DNA polymerase (Boehringer Mannheim). The reactions were performed in a PTC-100 thermal cycler (MJ research, Inc. Watertown, Mass.) for 40 cycles (94° C. for 30 seconds, 40° C. for 30 seconds, 72° C. for 2 minutes), followed by a 5 minute extension at 72° C.

EXAMPLE 2

Cloning and Characterization of the PCR Products

Following the PCR reactions described above, the PCR products were electrophoresed on an agarose gel and visualized by staining with ethidium bromide. PCR fragments with the expected sizes were purified using a GeneClean II kit (Bio 101, LaJolla, Calif.), and ligated into pT7Blue T-Vector (Novagen, Madison, Wis.). The ligation mixtures were used to transform *E. coli* DH5α competent cells which were then spread on LB agar plates containing 100 μg/ml ampicillin, 50 μg/ml X-Gal (5-bromo-4-chloro-3-indolyl-β-D-galactoside) and 1 mM IPTG. White colonies were screened by direct colony PCR using vector specific reverse (U19; Novagen U-19mer primer #69819-1) and forward (T7; Novagen promoter primer #6934-8-1) primers to detect the presence and size of inserts. Colonies containing inserts of the expected size were used to inoculate 3 ml of LB containing 100 μg/ml ampicillin and the cultures were incubated at 37° C. overnight to produce cells for plasmid DNA isolation. Plasmid DNA was purified using the Wizard kit (Promega, Madison, Wis.), and the sequences of the inserts were determined using the fmol PCR sequencing system (Promega) and the vector specific reverse (U19) and forward (T7) primers. The manufacturer's recommended protocol was used, except the annealing was done at a slightly higher temperature (50° C. for 30 seconds, instead of 42° C. for 30 seconds).

The sequences of the PCR products were compared with the sequences available in the GenBank and the Swiss Protein Bank databases, using the Multiple Sequence Alignment Program from the Lasergene System (DNAStar, Inc., Madison, Wis.) and the BLAST program (S. F. Altschul, et al., *J. Mol. Biol.* 215:403–410 (1990)) in the non-redundant DNA sequence Database at the National Center for Biotechnology Information (NCBI). The comparison confirmed that the nucleic acids from the PCR amplification encoded polypeptides having amino acid sequences similar to known tryptophanyl-tRNA synthetase amino acid sequences. The sequences of the PCR fragments were most similar to the cytoplasmic TrpRSs of *S. pombe* or *S. cerevisiae* (hypothetical protein HRE342). Results of the query are summarized in Table 2.

TABLE 2

RESULTS OF PCR AMPLIFICATIONS USING COMBINATIONS OF DEGENERATE PRIMERS DEFINED IN TABLE 1

| Primer Combination/ Fragment | Expected Size (bp) | PCR Product | Origin | Highest Similarity |
|---|---|---|---|---|
| CaW-4#/CaW-5# | 290 | + | cytoplasmic | *S. cerevisiae* hypothetical protein HRE342 |
| CaW-5#/CaW-1# | 700 | + | cytoplasmic | *S. cerevisiae* hypothetical protein HRE342 |
| CaW-5#/PCT-2 | 170 | + | | |
| CaW-4#/CaW-3# | 560 | + | | |

EXAMPLE 3

Cloning of the *Candida albicans* cytoplasmic TrpRS Gene by Semi-Specific PCR

The 5' and 3' ends of the *Candida albicans* TrpRS gene were each obtained following two rounds of semi-specific PCR. Amplifications were performed in a 50 μl reaction volume with 1× Taq polymerase buffer, 100 μM of each dNTP, 1 unit of Taq DNA polymerase (Boehringer-Mannheim) with the indicated amount of template DNA and primers.

First Semi-Specific PCR Reaction

Ten different non-specific primers were individually tested with each specific primer described in Table 3. PCR conditions were as follows: each tube contained 100 ng of *Candida albicans* genomic DNA, 40 pmole of specific primer, and 60 ng of one non-specific primer (see Table 3). After an initial incubation at 94° C. for 2 minutes, PCR products were generated in 30 successive cycles at 94° C. (30 seconds), 50° C. (30 seconds) and 72° C. (3 minutes), followed by a final extension step at 72° C. for 3 minutes.

TABLE 3

SPECIFIC AND NONSPECIFIC PRIMERS USED IN SEMI-SPECIFIC PCR REACTIONS FOR CLONING 5' AND 3' ENDS OF CANDIDA TrpRS GENE

| | Seq. ID NO: | Primer Sequence |
|---|---|---|
| A) For 3' end Specific Primer | | |
| CaW-6# | 6 | 5'-CGA TGT ATT AGG ATT ACC ACC-3' |
| CaW-7# | 7 | 5'-GGA TTA CCA CCA AAG ACC C-3' |
| CaW-10# | 8 | 5'-CAT CAT TCC CCG ATG TAT TAG G-3' |
| CaW-11# | 9 | 5'-CAT TTT TCA GTT ATG ATG ATG AAA-3' |
| B) For 5' end Specific Primer | | |
| CaW-8# | 10 | 5'-CAT AAT CAA TCC CCA TTG-3' |
| CaW-9# | 11 | 5'-GTC TAC AAC GGC ACC TTC TAC-3' |

TABLE 3-continued

SPECIFIC AND NONSPECIFIC PRIMERS USED IN SEMI-SPECIFIC PCR REACTIONS FOR CLONING 5' AND 3' ENDS OF CANDIDA TrpRS GENE

| | Seq. ID NO: | Primer Sequence |
|---|---|---|
| CaW-12# | 12 | 5'-GAT ATG TTT GGT ACC GAA TTG AC-3' |
| C) Non-specific Primer | | |
| Met JT1 | 13 | 5'-GGTGTACGTCTGGTTCGATG-3' |
| Met JT2 | 14 | 5'-ATCTCGCGCTTTGTTCGATC-3' |
| Met JT3 | 15 | 5'-GTATGGGATTGAAGAATTACGC-3' |
| Met JT4 | 16 | 5'-TACACCACATGTTTAGGATCGTTC-3' |
| Met JT5 | 17 | 5'-ACGAATCAGAAAACTAGAAGCC-3' |
| Met JT6 | 18 | 5'-CAATAACTCTCACAGCTCACGC-3' |
| Met JT7 | 19 | 5'-GTAGGGCTTATCAAAGAAGCTC-3' |
| Met JT10 | 20 | 5'-TAAATTAGCCACCACGCACACC-3' |
| Met JT11 | 21 | 5'-CGCACCACAGACAGCGAGCATC-3' |
| Met JT12 | 22 | 5'-CGGTGTCTTGTAAAACCATATC-3' |

Second Semi-Specific PCR Reaction

One μl of each of the 10 PCR products (without purification) from the first round of semi-specific PCR reactions was used as a template for amplification in the second round of semi-specific PCR, with 40 pmol of specific primer and 60 ng of one of the non-specific primers (see Table 3). The primer CaW-6# (SEQ ID NO:6) was used for the 3' end reactions and the primer CaW-8# (SEQ ID NO:10) was used for the 5' end reactions. The PCR products were generated by 30 cycles at 94° C. (30 seconds), 50° C. (30 seconds), 72° C. (3 minutes), followed by a final extension at 72° C. for 3 minutes.

Products of the second PCR reaction were separated by electrophoresis on a 1% agarose gel. Multiple bands from each reaction were visualized by uv-illumination of ethidium bromide-stained gel. Each PCR product was processed with the Wizard PCR Preparation Purification System Reagents (Promega) and sequenced with a specific internal primer (CaW-7# (SEQ ID NO:7) for the 3' and CaW-9# (SEQ ID NO:11) for the 5'end reactions) using the fmol PCR sequencing system (Promega). The recommended protocol was used, except that annealing was performed at a slightly higher temperature (50° C. for 30 seconds, instead of 42° C. for 30 seconds). Two of the PCR reactions yielded sequences containing the 3' end of the *Candida albicans* cytoplasmic TrpRS gene. Six of the PCR reactions yielded sequences containing the 5' end of the *Candida albicans* cytoplasmic TrpRS gene.

Two primers, CaW-13# (SEQ ID NO:23, less than 20 base pairs downstream from the stop codon) and CaW-14# (SEQ ID NO:24, less than 50 base pairs upstream from the start codon) were designed to clone the entire open reading frame from the SC5314 genomic DNA.

CaW-13#: 5'-ACT CTA CTA TAT AAA TAT GTA TCT CC-3'

CaW-14#: 5'-GAT AAT TAG TCA ATA TCT AAG TAC TG-3'

The PCR reaction was performed in a 50 μl volume with 200 ng of Candida albicans genomic DNA from strain SC5314, 40 pmoles of each primer, 10 mM Tris-HCl pH 8.3, 50 mM KCl, 1.5 mM MgCl$_2$, 100 μM of each dNTP, and 1 unit of Taq DNA polymerase (Boehringer Mannheim). The reaction was performed for 30 cycles (94° C. for 30 seconds, 55° C. for 30 seconds, 72° C. for 2 minutes), followed by a 3 minute extension at 72° C.).

Using the full-length PCR fragment, the entire gene was sequenced by the fmol PCR sequencing method (Promega). The recommended protocol was used, except the annealing was done at a slightly higher temperature (50° C. for 30 seconds, instead of 42° C. for 30 seconds). At each round of sequencing, primers designed from sequence information obtained at the previous rounds of sequencing were used. The sequence within the ORF of the C. albicans TrpRS was determined for both DNA strands. The individual sequences obtained at each round of sequencing were assembled using the DNA Sequence Management Program of the DNASTAR package to generate contiguous sequences. The methionine initiation codon was identified by comparison with sequences of corresponding TrpRS genes present in the GenBank, using the Multiple Sequence Alignment program from the DNASTAR package.

EXAMPLE 4

Nucleotide Sequence and Deduced Amino Acid Sequence of C. albicans Cytoplasmic TrpRS Gene The 1366 nucleotide sequence containing the C. albicans cytoplasmic tryptophanyl-tRNA synthetase gene (TrpRS or CaTrpRS) is shown in FIG. 1A–1B (SEQ ID NO: 25). The ORF is 1275 base pairs and encodes a polypeptide of 425 amino acids (SEQ ID NO:26), with translation starting at the ATG at position 30. The amino acid sequence deduced from the TrpRS gene contains two characteristic peptide motifs present in all class I synthetases ($^{109}$HLGH$^{112}$ and $^{287}$KMSAS$^{291}$). The sequence of degenerate primer CaW-1# (SEQ ID NO:1) was found to correspond to nucleotides 78–98 of SEQ ID NO:25; the sequence of degenerate primer CaW-5# (SEQ ID NO:4) was found to correspond to nucleotides 765–785 of SEQ ID NO:25. Four bases could not be identified unambigously: nucleotides 122, 410 AND 1202 are marked as Y (=T or C) and nucleotide 1007 is marked as R (=A or G). These ambiguities in the sequence do not affect the amino acid sequence deduced from the TrpRS gene. The percent similarity between the nucleic acid sequence of the C. albicans cytoplasmic TrpRS and the protein identified as HRE342 from S. cerevisiae was determined using the Multiple Sequence Alignment Program of the Lasergene System (DNAStar, Inc., Madison, Wis.) using the Clustal method with the PAM250 residue weight table using default parameters and was found to be 57%.

Candida albicans uses a non-universal genetic code; the codon CUG, which normally codes for leucine in most organisms, including S. cerevisiae, codes for serine in several species of Candida (Ohama, T., et al., Nucleic Acids Res. 17:4039–4046 (1993)). There are no CUG codons in the sequence determined for the Candida albicans TrpRS ORF.

The C. albicans TrpRS amino acid sequence was compared with the TrpRS sequences available in GenBank by using the Multiple Sequence Alignment Program of the Lasergene System (DNAStar, Inc., Madison, Wis.); percent similarity and percent divergence among these sequences were determined using the Clustal method with the PAM250 residue weight table using default parameters and was found to be 57%. The percent similarity between the predicted amino acid sequence of the C. albicans cytoplasmic TrpRS and the protein identified as HRE342 from S. cerevisiae was found to be 74%. The percent similarities to the S. pombe or human TrpRS sequences were found to be 62% and 51%, respectively.

EXAMPLE 5

Expression of C. albicans Tryptophanyl-tRNA Synthetase in E. coli

Several constructs were made using the pGEX-4T-2 (Pharmacia) or pCYB2 (New England Biolabs) expression vectors for expression in E. coli and purification of the TrpRS cytoplasmic protein. Plasmid pC$^3$821 and pC$^3$822 express GST-TrpRS fusion proteins. The GST moiety in these fusions can be cleaved off using a thrombin cleavage site at the junction of GST and TrpRS resulting in a recombinant protein with 2 (Gly, Ser from pC$^3$821) or 3 (Gly, Ser, His from pC$^3$822) additional N-terminal amino acid residues. A third construct, pC$^3$823, designed to express a native form of Candida albicans cytoplasmic TrpRS gene using the IMPACT system (New England Biolabs) was also tested.

Expression Constructs

A) Cytoplasmic TrpRS As an N-terminal GST-fusion in pGEX-4T-2 (Pharmacia)

The ends of a 1.3 kb fragment comprising the gene for the C. albicans TrpRS were modified by PCR using specifically designed primers to facilitate cloning into the BamHI-XhoI sites of pGEX-4T-2 (Pharmacia). The 5' PCR primer (CaW-5'B :5'-CGC GGA TCC ATG TCA GTT GAA GAA 3' (SEQ ID NO:27)) introduced a BamHI cleavage site immediately upstream from the ATG initiation codon, while the 3' primer (CaW-3'X: 5'-CCG CTC GAG TTA CTT TTT GGC TTT C-3' (SEQ ID NO:28)) introduced an XhoI cleavage site immediately following the TAA termination codon. PCR amplifications were carried out in 50 ul with 2 units of Vent DNA polymerase (New England Biolabs) and in the presence of 1× Vent DNA polymerase buffer, 100 uM of each dNTP, 2 μM of each primer and 100 ng of SC 5314 genomic DNA template, for 30 cycles of 94° C. (30 seconds), 60° C. (30 seconds), and 72° C. (90 seconds). The 1.3 kb PCR fragment produced by this reaction was purified with the Wizard PCR Purification kit, digested with BamHI and XhoI restriction enzymes, purified again (1.5% Low melting point agarose gel followed by collecting the eluate from the gel slice through a SpinX centrifuge tube filter, catalog number 8162 (0.435 μm) cellulose acetate column (Costar)), and ligated into BamHI/XhoI digested pGEX-4T-2 expression vector (Pharmacia), yielding plasmid pC$^3$821.

B) PCR-directed Mutagenesis to remove the NdeI site in C. albicans Cytoplasmic TrpRS Gene and Expression in pGEX-4T-2NdeI and pCYB2

A construct using a modified pGEX-4T-2 vector was prepared. To make pGEX-4T-2NdeI, pGEX-4T-2 was linearized with BamHI and EcoRI followed by purification by agarose gel and the GeneClean kit (Bio 101). The linearized pGEX-4T-2 DNA was then ligated with 5' phosphorylated oligonucleotides pGEX-A (5'-GATCCCATATGGG) (SEQ ID NO:29) and pGEX-B (5'-AATTCCCATATGG) (SEQ ID NO:30), at about a 20-fold excess of the plasmid DNA which were annealed to each other by incubating for 2 minutes at 85° C., and 15 minutes each at 65° C., 37° C., 25° C., and 0° C. in sequential order. The resultant plasmids were transformed into E. coli DH5α cells (competent cells purchased from Gibco/BRL). The plasmids were isolated from the transformants and characterized with restriction endonuclease mapping and DNA sequencing. The desired construct, pGEX-4T-2NdeI, was identified and was characterized as identical to pGEX-4T-2 except that it contained the following DNA sequence between the BamHI site and EcoRI site, which introduces a NdeI site with its ATG codon in-frame with the glutathione S-transferase coding sequence: ggatccCATATGGgaattc (SEQ ID NO:31).

PCR mutagenesis had to be used to remove an internal NdeI site in the gene between positions 363–368. Vent DNA polymerase (using a standard PCR reaction cocktail on 100 ng of Candida genomic DNA SC5314 as template) was employed to generate two overlapping PCR fragments in a first round of mutagenesis. CaW-18# and CaW-23# primers were designed to change the base at position 365 from T to C in order to remove the internal NdeI recognition site without altering the encoded amino acid sequence. CaW-18#(SEQ ID NO:30) corresponds to nucleotides 340–385 of the non-coding strand of SEQ ID NO:25:

5'-GTAAATATAAATGGTACCATgTGAC-
CCAAATGCATTGAATCAGATG-3'

CaW-23#(SEQ ID NO:33) corresponds to nucleotides 353–392 of coding strand of SEQ ID NO:25:

5'-GCATTTGGGTCAcATGGTACCATTTATATTTACAAAATGG-3'

CaW-18# was used with CaW-5'N (5'-GGG AAT TC C ATA TGT CAG TTG AAG AA-3', (SEQ ID NO:34, 5' primer for cloning in pGEX-4T-2NdeI expression vector). CaW-23# was used with either CaW-3'X (SEQ ID NO:28, 3' primer for cloning in pGEX-4T-2NdeI expression vector) or CAW-3'X-TC (5'-CCG CTCGAG CTT TTT GGC TTT C-3' (SEQ ID NO:35)), 3' primer for cloning in pCYB2 expression vector).

The mixture was heated to 94° C. for 2 min followed by 30 cycles at (94° C. (30 sec), 55° C., (30 sec) and (72° C., (90 seconds) followed by 5 minutes extension at 72° C. PCR fragments from this round of PCR were gel purified and used as template for a second PCR reaction, employing only CaW-5'N and either CaW-3'X or CaW-3'X-TC primers, but otherwise with PCR conditions identical to the previous round.

The PCR fragments were processed with the Wizard PCR Preparation Purification System Reagents (Promega), digested with NdeI and XhoI restriction enzymes, run on a 1% agarose gel and purified using the GENECLEAN II kit. The resulting DNA fragments were cloned into NdeI/XhoI digested pGEX-4T-2/NdeI or pCYB2 expression vectors, yielding plasmid pC$^3$822 or pC$^3$823, respectively.

The C. albicans cytoplasmic TrpRS expression constructs pC$^3$821, pC$^3$822 and pC$^3$823 were used to transform E. coli DH5α MAX efficiency competent cells (Gibco BRL). E. coli transformants containing the correct insert were identified by colony PCR.

Single colonies from each transformation were transferred to LB+amp and incubated at 37° C. overnight. The overnight cultures were used to inoculate fresh LB+amp medium which was incubated at 37° C. until the cultures reached an OD$_{600}$ of 0.7 to 1.5. IPTG was added to a final concentration of 0.1 mM and the cells were shifted to 18° C. overnight, harvested by centrifugation, then lysed by sonication. The fusion proteins were purified by affinity chromatography and tested for tryptophanyl-tRNA synthetase activity (see Example 6). An extract of cells containing pGEX-4T-2 was used as a control. All three constructs gave active protein. Affinity-purified fusion protein produced in DH5α(pC$^3$821) and DH5α(pC$^3$822) appeared on SDS-polyacrylamide gels above the 66 kD protein marker, consistent with their expected size of 74 kD. The level of the fusion protein expressed from pC$^3$822 seemed higher than pC$^3$823 in the pilot expression experiments. The expression construct pC$^3$822 was sequenced to verify that the PCR mutagenesis procedure was successful. Besides the T365C change that was introduced to remove the NdeI site, the expression construct had one additional silent change at position 1013 (an A was changed to G) that may have been introduced inadvertently during the mutagenesis steps.

EXAMPLE 6

Purification and Enzymatic Characterization of Cytoplasmic TrpRS Fusion Protein pC$^3$822 was introduced into E. coli strain JM109 and pC$^3$822/JM109 strain was used for subsequent protein purification work.

A. Purification

Two liters of cells were grown in LB+amp at 37° C. until late log phase, and expression was induced by the addition of IPTG to 0.1 mM and incubation for 2 hr at 37° C., and then for overnight at 18° C. Cells were harvested and resuspended in cold PBS buffer containing 5 mM DTT, 100 µg/ml lysozyme, 1 mM phenylmethylsulfonyl fluoride (PMSF) and other protease inhibitors (5 µg/ml each of leupeptin, pepstatin, chymostatin and papain), and lysed by 2 passages through a French pressured cell.

Following cell lysis, whole cell extracts of JM109/pC$^3$822 were clarified by centrifugation at 20,000×g for 30 minutes at 4° C. GST-fusion proteins were purified by affinity chromatography on Glutathione Sepharose 4B resin (Pharmacia) equilibrated with PBS. Cell extracts were filtered through a 0.45 µ filter (Nalgene) and mixed with the resin in batch. Unbound proteins were washed off the resin with ice cold PBS (10 bed volumes) and bound proteins were incubated in 1× thrombin cleavage buffer with 25 units of biotinylated thrombin (Novagen) for 4 hours at room temperature and overnight at 4° C. The reaction mixture was filtered through a 0.45µ filter (Nalgene) and mixed with 400 µl of streptavidin agarose for one hour at room temperature to remove thrombin. The cleaved fusion protein was filtered once again, then concentrated by ultrafiltration using centrifuge concentrators (Centiprep 10 from Amicon), and stored at pH 7.5 at −20° C. in 40% glycerol in the presence of 5 mM DTT. Proteins were visualized on a 10% SDS-polyacrylamide gel following staining with Coomassie blue. The purity of the GST-TrpRS was estimated to be at least about 90%.

B. Enzymatic activity

The purified recombinant protein obtained after thrombin cleavage of the GST-fusion protein produced by JM109/pC$^3$822 was used for further kinetic studies. Charging assays were based on the procedure of Shepard et al. (*Proc. Natl. Acad. Sci. USA* 89:9964–68 (1992)). Unless otherwise stated, a typical 50 µl reaction, carried out at 25° C., contained 1 mM ATP, 1 µM of [$^3$H]Tryptophan (22.2 Ci/mmol), 90 µM crude tRNA from brewer's yeast (Boehringer Mannheim), 10 mM KF, 30 mM HEPES, 30 mM KCl pH 7.5, 5 mM MgCl$_2$, and 10 mM DTT. Purified enzyme was diluted in 100 mM HEPES, pH 7.5, 20 mM DTT and 0.1 mg/ml BSA.

Reactions were started by the addition of enzyme to the reaction mixture preincubated at 25° C., with 2.5 to 10 mn protein in the assay. At various time intervals, 10 µl of the reaction mix was quenched in a 96-well filter plate (Millipore, cat# MAFBNOB50) prefilled with 100 µl of cold 5% TCA. The liquid in the filter plate was drained by applying vacuum suction on the manifold. The plate was subsequently washed 2 times with 200 µl 5% TCA, 2 times with 100 µl double distilled H$_2$O with continuous vacuum suction, and once with 100 μl 95% EtOH. The plate was heat-dried under vacuum, 100 μl Microscint was added to each well, and the aminoacylated tRNA was quantitated by scintillation counting in a Topcount (Packard) scintillation counter. Results are shown in FIG. 2. Filled circles, recombinant cytoplasmic TrpRS at 1:2,000 dilution; filled squares, recombinant cytoplasmic TrpRS at 1:4,000 dilution; filled diamonds, recombinant cytoplasmic TrpRS at 1:8,000 dilution; open circles, native cytoplasmic TrpRS obtained from cell extract from *C. albicans* strain 90028, prepared as described in Example 7, at 1:40 dilution; open squares, native cytoplasmic TrpRS at 1:80 dilution; open diamonds, native cytoplasmic TrpRS at 1:160 dilution. The results show comparable profiles of charging between the native and the recombinant enzyme.

For determination of $K_m$, various concentrations of one substrate (ATP, amino acid, or tRNA) were used while the other two substrates were kept at saturating concentrations. Thrombin-treated *C. albicans* GST-tryptophanyl-tRNA synthetase enzyme had an apparent molecular weight of 48 kD as assessed by SDS-PAGE. The purified enzyme (with or without the GST moiety) was able to efficiently aminoacylate yeast total tRNAs. The $K_m$ for tryptophan was determined using crude yeast tRNA (Boehringer Mannheim) and 1 to 40 μM of [$^3$H]tryptophan. The $K_m$ value was 3–4 μM. $K_m$ was approximately 1.1 mM for ATP (concentration range from 0.19 to 6 mM).

EXAMPLE 7

Aminoacylation Activity of Cytoplasmic TrpRS Isolated from *C. albicans*

For *C. albicans* cytoplasmic tryptophanyl-tRNA synthetase, the kinetic values of the naturally occurring enzyme compare well to those of the recombinant enzymes (6 μM for tryptophan and 1.2 mM for ATP).

Preparation of 100S supernatant

Tryptophanyl-tRNA synthetase activities were tested directly in crude extracts obtained by mechanical cell breakage using glass beads (described by S. M. Jazwinski "Preparation of Extracts from Yeast" in "Guide to Protein Purification," by M. P. Deutscher (editor) *Methods in Enzymology* volume 182, Academic Press, Inc. (1990)). A single colony of the *Candida albicans* strain 90028 (ATCC Accession No. 90028) was grown in YEPD to saturation (30° C., 2 days). 5 μl of this saturated culture was used as inoculum for one liter of YPD broth in a 2 liter flask. Incubation was carried out at 30° C. overnight in a shaking incubator (225 rpm). Log-phase cells ($OD_{600}$=8–10) were harvested by low-speed centrifugation (3,000 rpm for 5 min). The cell pellet was washed (with distilled $H_2O$ or 100 mM Tris, pH 7.4) and resuspended as a 40% cell paste in chilled buffer A (20 mM $KPO_4$, pH 7.4) or 20 mM NaCl, pH 8.0, 10% glycerol, 5 mM DTT and 1–2 "Complete" tablets (a cocktail of protease inhibitors from Boehringer-Mannheim; Catalog Number 1697498).

Cells were broken after addition of an equal volume of glass beads (0.45 micron in diameter; Biospecs) in a Bead-Beater (Biospecs) with 1 min pulses and 1 min cooling periods at 4° C. Total breakage time varied depending on the efficiency of lysis. The cell breakage was followed by preparation of a 100S supernatant (by an initial low speed spin at 17,000 rpm for 30 min), to remove cell debris and glass beads, followed by a high speed spin at 36,500 rpm for 1 hour (100,000 g) by ultracentrifugation in a 70Ti rotor. The 100S supernatant was collected after two centrifugation steps; the conductivity and pH of the supernatant were adjusted before application onto the DEAE column (DEAE Sepharose Fast Flow (Pharmacia LKB Biotechnology)).

Aminoacylation Assays

Aminoacylation reactions were carried out at 25° C. in 30 mM HEPES pH 7.5, 30 mM KCl, 5 mM $MgCl_2$, 10 mM DTT, 20 μM [$^3$H]amino acid, 90 μM brewer's yeast tRNA (Boehringer-Mannheim Biochemicals, Inc.), 2 mM ATP, 10 mM KF, and a suitable dilution of the partially purified enzyme from *C. albicans*. 15 μl of each reaction were quenched in a 96-well filter plate and processed as detailed above. The cytoplasmic TrpRS activity was more stable if the 100S supernatant was purified by a DEAE column. Elution was done with 500 mM NaCl or potassium phosphate, using a gradient or a step-wise elution. In gradient elution the salt concentration was increased gradually from 20 mM to 500 mM. In step-wise elutions, the salt concentration was stepped up from 20 mM first to 300 mM, then to 500 mM. Fractions containing TrpRS activity were pooled and concentrated, and stored at −20° C. in 40% glycerol. The activity has remained stable over an 8 month period.

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. An isolated nucleic acid which encodes at least a functional portion of a *Candida albicans* cytoplasmic tryptophanyl-tRNA synthetase, said portion having catalytic activity or binding function.

2. An isolated nucleic acid which encodes a cytoplasmic tryptophanyl-tRNA synthetase having the amino acid sequence of a cytoplasmic tryptophanyl-tRNA synthetase isolated from *Candida albicans*.

3. An isolated nucleic acid having the sequence of a nucleic acid isolated from *Candida albicans* and encoding a cytoplasmic tryptophanyl-tRNA synthetase.

4. An isolated nucleic acid which encodes the amino acid sequence SEQ ID NO:26.

5. A vector comprising a nucleic acid which encodes a polypeptide comprising at least a functional portion of a *Candida albicans* cytoplasmic tryptophanyl-tRNA synthetase, said functional portion having catalytic activity or binding function.

6. The vector of claim 5, wherein the polypeptide further comprises glutathione S-transferase.

7. A host cell comprising a recombinant nucleic acid which encodes a polypeptide comprising a *Candida albicans* cytoplasmic tryptophanyl-tRNA synthetase or a functional portion thereof, said functional portion having catalytic activity or binding function.

8. A host cell comprising a recombinant nucleic acid vector which encodes a polypeptide comprising a *Candida albicans* cytoplasmic tryptophanyl-tRNA synthetase or a functional portion thereof, said functional portion having catalytic activity or binding function.

9. An expression vector comprising a nucleic acid encoding a fusion protein comprising a *Candida albicans* cytoplasmic tryptophanyl-tRNA synthetase or a functional portion thereof, said functional portion having catalytic activity or binding function, wherein said nucleic acid comprises all or part of the coding sequence for a *Candida albicans* cytoplasmic tryptophanyl-tRNA synthetase, and wherein the coding sequence is operably linked to one or more expression control sequences.

10. A method for producing a polypeptide comprising a *Candida albicans* cytoplasmic tryptophanyl-tRNA synthetase or a functional portion thereof, said functional portion having catalytic activity or binding function, said method comprising:

a) constructing a recombinant nucleic acid vector comprising a nucleic acid encoding a polypeptide comprising a *Candida albicans* cytoplasmic tryptophanyl-tRNA synthetase wherein the coding sequence is under the control of transcription signals and is linked to appropriate translation signals;

b) introducing the vector into host cells which support the replication of the vector; and c) maintaining the host cells under conditions in which the polypeptide is expressed.

11. A method for producing a *Candida albicans* cytoplasmic tryptophanyl-tRNA synthetase or a functional portion thereof, said functional portion having catalytic or binding function, comprising the steps of introducing a recombinant nucleic acid vector comprising a nucleic acid encoding a *Candida albicans* cytoplasmic tryptophanyl-tRNA synthetase or functional portion thereof into host cells, and maintaining the host cells under conditions in which the nucleic acid is expressed.

12. A method for producing a polypeptide comprising a *Candida albicans* cytoplasmic tryptophanyl-tRNA synthetase or a functional portion thereof, said functional portion having catalytic or binding function, comprising maintaining a host cell comprising a recombinant nucleic acid encoding said polypeptide under conditions suitable for expression of the nucleic acid, whereby the encoded polypeptide is expressed and thereby produced.

13. The method of claim 12 further comprising the step of isolating the polypeptide.

14. The method of claim 12 wherein the polypeptide further comprises glutathione S-transferase.

15. A method for producing a polypeptide comprising a Candida cytoplasmic tryptophanyl-tRNA synthetase or a functional portion thereof, said functional portion having catalytic activity or binding function, comprising maintaining a host cell comprising a recombinant nucleic acid encoding said polypeptide under conditions suitable for expression of the nucleic acid, whereby the encoded polypeptide is expressed and thereby produced, and recovering said polypeptide.

16. An isolated nucleic acid comprising a sequence sharing at least about 90% nucleotide sequence identity with SEQ ID NO: 25, and encoding at least a portion of a *Candida albicans* cytoplasmic tryptophanyl-tRNA synthetase having catalytic or binding function.

17. An isolated nucleic acid sharing at least about 90% nucleotide sequence identity with SEQ ID NO: 25, and encoding at least a portion of a *Candida albicans* cytoplasmic tryptophanyl-tRNA synthetase having catalytic or binding function.

18. An isolated nucleic acid comprising a sequence sharing at least about 95% nucleotide sequence identity with SEQ ID NO: 25, and encoding at least a portion of a *Candida albicans* cytoplasmic tryptophanyl-tRNA synthetase having catalytic or binding function.

19. An isolated nucleic acid sharing at least about 95% nucleotide sequence identity with SEQ ID NO: 25, and encoding at least a portion of a *Candida albicans* cytoplasmic tryptophanyl-tRNA synthetase having catalytic or binding function.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 9

(D) OTHER INFORMATION: /mod_base= i (ix) FEATURE:
              (A) NAME/KEY: modified_base
              (B) LOCATION: 12
              (D) OTHER INFORMATION: /mod_base= i (ix) FEATURE:
              (A) NAME/KEY: modified_base
              (B) LOCATION: 15
              (D) OTHER INFORMATION: /mod_base= i (ix) FEATURE:
              (A) NAME/KEY: modified_base
              (B) LOCATION: 18
              (D) OTHER INFORMATION: /mod_base= i (xi) SEQUENCE DESCRIPTION: SEQ ID NO:1:

GARCARRTNG TNACNCCNTG G                                              21

(2) INFORMATION FOR SEQ ID NO:2:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ix) FEATURE:
              (A) NAME/KEY: modified_base
              (B) LOCATION: 6
              (D) OTHER INFORMATION: /mod_base= i (ix) FEATURE:
              (A) NAME/KEY: modified_base
              (B) LOCATION: 12
              (D) OTHER INFORMATION: /mod_base= i (ix) FEATURE:
              (A) NAME/KEY: modified_base
              (B) LOCATION: 18
              (D) OTHER INFORMATION: /mod_base= i (ix) FEATURE:
              (A) NAME/KEY: modified_base
              (B) LOCATION: 21
              (D) OTHER INFORMATION: /mod_base= i (xi) SEQUENCE DESCRIPTION: SEQ ID NO:2:

ACRTCNACRT CNGGRTTNCC NCC                                            23

(2) INFORMATION FOR SEQ ID NO:3:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ix) FEATURE:
              (A) NAME/KEY: modified_base
              (B) LOCATION: 9
              (D) OTHER INFORMATION: /mod_base= i (xi) SEQUENCE DESCRIPTION: SEQ ID NO:3:

GARAAYGCNA ARGAYAT                                                   17

(2) INFORMATION FOR SEQ ID NO:4:

(i) SEQUENCE CHARACTERISTICS:
              (A) LENGTH: 23 base pairs
              (B) TYPE: nucleic acid
              (C) STRANDEDNESS: single (D) TOPOLOGY: linear (ix) FEATURE:
            (A) NAME/KEY: modified_base
            (B) LOCATION: 15
            (D) OTHER INFORMATION: /mod_base= i (ix) FEATURE:
            (A) NAME/KEY: modified_base
            (B) LOCATION: 21
            (D) OTHER INFORMATION: /mod_base= i (xi) SEQUENCE DESCRIPTION: SEQ ID NO:4:

GGRTCYTGRT CDATNGCRCA NGG                                              23

(2) INFORMATION FOR SEQ ID NO:5:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 12
            (D) OTHER INFORMATION: /mod_base= i (ix) FEATURE:
            (A) NAME/KEY: modified_base
            (B) LOCATION: 18
            (D) OTHER INFORMATION: /mod_base= i (ix) FEATURE:
            (A) NAME/KEY: modified_base
            (B) LOCATION: 21
            (D) OTHER INFORMATION: /mod_base= i (xi) SEQUENCE DESCRIPTION: SEQ ID NO:5:

TTYAAYCARG TNAARGGNAT NTTYGG                                           26

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:6:

CGATGTATTA GGATTACCAC C                                                21

(2) INFORMATION FOR SEQ ID NO:7:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:7:

GGATTACCAC CAAAGACCC                                                   19

(2) INFORMATION FOR SEQ ID NO:8:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:8:

CATCATTCCC CGATGTATTA GG                                                          22

(2) INFORMATION FOR SEQ ID NO:9:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:9:

CATTTTTCAG TTATGATGAT GAAA                                                        24

(2) INFORMATION FOR SEQ ID NO:10:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:10:

CATAATCAAT CCCCATTG                                                               18

(2) INFORMATION FOR SEQ ID NO:11:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:11:

GTCTACAACG GCACCTTCTA C                                                           21

(2) INFORMATION FOR SEQ ID NO:12:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:12:

GATATGTTTG GTACCGAATT GAC                                                         23

(2) INFORMATION FOR SEQ ID NO:13:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:13:

GGTGTACGTC TGGTTCGATG                                                             20

(2) INFORMATION FOR SEQ ID NO:14:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:14:

```
ATCTCGCGCT TTGTTCGATC                                                    20
```

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:15:

```
GTATGGGATT GAAGAATTAC GC                                                 22
```

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:16:

```
TACACCACAT GTTTAGGATC GTTC                                               24
```

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:17:

```
ACGAATCAGA AAACTAGAAG CC                                                 22
```

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:18:

```
CAATAACTCT CACAGCTCAC GC                                                 22
```

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:19:

```
GTAGGGCTTA TCAAAGAAGC TC                                                 22
```

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:20:

```
TAAATTAGCC ACCACGCACA CC                                               22

(2) INFORMATION FOR SEQ ID NO:21:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:21:

CGCACCACAG ACAGCGAGCA TC                                               22

(2) INFORMATION FOR SEQ ID NO:22:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:22:

CGGTGTCTTG TAAAACCATA TC                                               22

(2) INFORMATION FOR SEQ ID NO:23:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO:23:

ACTCTACTAT ATAAATATGT ATCTCC                                           26

(2) INFORMATION FOR SEQ ID NO:24:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO:24:

GATAATTAGT CAATATCTAA GTACTG                                           26

(2) INFORMATION FOR SEQ ID NO:25:

(i) SEQUENCE CHARACTERISTICS:
         (A) LENGTH: 1366 base pairs
         (B) TYPE: nucleic acid
         (C) STRANDEDNESS: double
         (D) TOPOLOGY: linear (xi) SEQUENCE DESCRIPTION: SEQ ID NO:25:

TAGAATATAA ATCACTCCAC ATTTCATTAA TGTCAGTTGA AGAAAAAGTA TCACAGCTCA       60

AAGTTACTGA GGAGTCAGAA CAAAAAATCA CTCCATGGGA AGTAGAAGGT GCCGTTGTAG      120

AYGGGAAATC AATGGGGATT GATTATGATA AATTAATTAG TCAATTCGGT ACCAAACATA      180

TCACTGAGGA AACATTAGAA AGATTTAAAC AAGTTACTGG TGAAGAGCCT CATCCATTTT      240

TGAAAAGAGG AGTATTTTTT TCACAAAGAG ATTTAGATCG TATTTTAGAT TTATATGAAC      300

ACGGAGAACC ATTCTTTTTA TATACTGGAA GAGGTCCATC ATCTGATTCA ATGCATTTGG      360

GTCATATGGT ACCATTTATA TTTACAAAAT GGTTACAAGA AGTATTTGAY GTCCCATTAG      420
```

-continued

```
TTATTGAATT AACTGATGAT GAGAAATTTT TATTTAAACA CCAATTAACT ATTGATGATG      480

TTAAAGGTTT TGCCGCAGAA AATGCTAAAG ATATAATTGC CGTTGGATTC AATCCGGAAA      540

ATACATTTAT CTTTTCAGAT TTACAATATA TGGGTGGAGC ATTTTATGAA AACGTCGTTA      600

GAACATCACG TCAAATCACT ACTTCTACAG CTAAAGCAGT ATTTGGATTC ACTGATTCTG      660

ATTGTATTGG GAAATACAT TTTGCAAGTA TTCAAATAGC AACTGCATTC CCATCATCAT       720

TCCCCGATGT ATTAGGATTA CCACCAAAGA CCCCTTGTTT AATTCCTTGT GCCATAGATC      780

AAGATCCTTA TTTTAGAGTT TGTAGAGATG TTGCCGATAA ATTAAGATTT ACCAAACCAG      840

CATTAATTCA TGCTAAATTT TTCCCAGCTT TACAAGGGGC ATCGACAAAA ATGTCAGCTT      900

CTGATACTAC AACTTCGATT TTCATGGGTG ATACAGCAAA ACAAATTCAG AAAAAAATTA      960

ATAAATATGC ATTTTCCGGT GGTAGAGCCA CTGCTGAAGA ACATCGRGAA TTAGGAGGTA     1020

ACCCAGAAGT AGATGTTGCA TTCCAATATT TATCATTTTT CAGTTATGAT GATGAAAAAT     1080

TGGCACAATT AGAACAAGGT TATAGAAAGG GAGAAATATT ATCAGGAGAA ATGAAAAAAG     1140

AATGTATTAC AGTTTTACAA GAATTTGTAT CTGCTTATCA AGAAAGAAGA AGTAAAGTTG     1200

AYGACCAAGT TGTTGAAAAA TTCATGAAAC CACATAAATT GGTGTTTGGT AATAAGGAAA     1260

GAAAAGTTCC TGCCAAACAA AGAGAAAAGA AAGCCAAAAA GTAAATCAGG CTTGAATACA     1320

ATGGAGATAC ATATTTATAT AGTAGAGTAA TCTATAGATA TTAATT                   1366
```

(2) INFORMATION FOR SEQ ID NO:26:

(i) SEQUENCE CHARACTERISTICS:
        (A) LENGTH: 424 amino acids
        (B) TYPE: amino acid
        (C) STRANDEDNESS:
        (D) TOPOLOGY: linear (xi) SEQUENCE DESCRIPTION: SEQ ID NO:26:

```
Met Ser Val Glu Glu Lys Val Ser Gln Leu Lys Val Thr Glu Glu Ser
1               5                   10                  15

Glu Gln Lys Ile Thr Pro Trp Glu Val Glu Gly Ala Val Val Asp Gly
            20                  25                  30

Lys Ser Met Gly Ile Asp Tyr Asp Lys Leu Ile Ser Gln Phe Gly Thr
        35                  40                  45

Lys His Ile Thr Glu Glu Thr Leu Glu Arg Phe Lys Gln Val Thr Gly
    50                  55                  60

Glu Glu Pro His Pro Phe Leu Lys Arg Gly Val Phe Ser Gln Arg
65                  70                  75                  80

Asp Leu Asp Arg Ile Leu Asp Leu Tyr Glu His Gly Glu Pro Phe Phe
                85                  90                  95

Leu Tyr Thr Gly Arg Gly Pro Ser Ser Asp Ser Met His Leu Gly His
            100                 105                 110

Met Val Pro Phe Ile Phe Thr Lys Trp Leu Gln Glu Val Phe Asp Val
        115                 120                 125

Pro Leu Val Ile Glu Leu Thr Asp Asp Glu Lys Phe Leu Phe Lys His
    130                 135                 140

Gln Leu Thr Ile Asp Asp Val Lys Gly Phe Ala Ala Glu Asn Ala Lys
145                 150                 155                 160

Asp Ile Ile Ala Val Gly Phe Asn Pro Glu Asn Thr Phe Ile Phe Ser
                165                 170                 175

Asp Leu Gln Tyr Met Gly Gly Ala Phe Tyr Glu Asn Val Val Arg Thr
            180                 185                 190
```

-continued

```
Ser Arg Gln Ile Thr Thr Ser Thr Ala Lys Ala Val Phe Gly Phe Thr
        195                 200                 205

Asp Ser Asp Cys Ile Gly Lys Ile His Phe Ala Ser Ile Gln Ile Ala
        210                 215                 220

Thr Ala Phe Pro Ser Ser Phe Pro Asp Val Leu Gly Leu Pro Pro Lys
225                 230                 235                 240

Thr Pro Cys Leu Ile Pro Cys Ala Ile Asp Gln Asp Pro Tyr Phe Arg
                245                 250                 255

Val Cys Arg Asp Val Ala Asp Lys Leu Arg Phe Thr Lys Pro Ala Leu
            260                 265                 270

Ile His Ala Lys Phe Phe Pro Ala Leu Gln Gly Ala Ser Thr Lys Met
        275                 280                 285

Ser Ala Ser Asp Thr Thr Thr Ser Ile Phe Met Gly Asp Thr Ala Lys
        290                 295                 300

Gln Ile Gln Lys Lys Ile Asn Lys Tyr Ala Phe Ser Gly Gly Arg Ala
305                 310                 315                 320

Thr Ala Glu Glu His Arg Glu Leu Gly Gly Asn Pro Glu Val Asp Val
                325                 330                 335

Ala Phe Gln Tyr Leu Ser Phe Phe Ser Tyr Asp Asp Glu Lys Leu Ala
            340                 345                 350

Gln Leu Glu Gln Gly Tyr Arg Lys Gly Glu Ile Leu Ser Gly Glu Met
        355                 360                 365

Lys Lys Glu Cys Ile Thr Val Leu Gln Glu Phe Val Ser Ala Tyr Gln
        370                 375                 380

Glu Arg Arg Ser Lys Val Asp Asp Gln Val Val Glu Lys Phe Met Lys
385                 390                 395                 400

Pro His Lys Leu Val Phe Gly Asn Lys Glu Arg Lys Val Pro Ala Lys
                405                 410                 415

Gln Arg Glu Lys Lys Ala Lys Lys
                420
```